US008440204B2

(12) United States Patent
Johnson et al.

(10) Patent No.: US 8,440,204 B2
(45) Date of Patent: May 14, 2013

(54) SUBTYPE OF *CLOSTERIDIUM BOTULINUM* NEUROTOXIN TYPE A AND USES THEREOF

(75) Inventors: Eric A. Johnson, Madison, WI (US); Mark Joseph Jacobson, Madison, WI (US); Guangyun Lin, Madison, WI (US); Raymond C. Stevens, La Jolla, CA (US); Jerome Dupuy, Saint Quentin sur Isere (FR); Pål Erik Gustav Stenmark, Stockholm (SE); William H. Tepp, Stoughton, WI (US)

(73) Assignees: Wisconsin Alumni Research Foundation, Madison, WI (US); The Scripps Research Institute, La Jolla, CA (US)

( * ) Notice: Subject to any disclaimer, the term of this patent is extended or adjusted under 35 U.S.C. 154(b) by 160 days.

(21) Appl. No.: 12/769,754

(22) Filed: Apr. 29, 2010

(65) Prior Publication Data
US 2011/0171226 A1 Jul. 14, 2011

Related U.S. Application Data

(60) Provisional application No. 61/174,331, filed on Apr. 30, 2009.

(51) Int. Cl.
| C07K 14/33 | (2006.01) |
| C07K 16/12 | (2006.01) |
| C07H 21/00 | (2006.01) |
| A61K 39/40 | (2006.01) |
| A61K 38/16 | (2006.01) |
| C12P 21/08 | (2006.01) |
| C12P 21/00 | (2006.01) |
| G01N 33/68 | (2006.01) |
| A61P 25/00 | (2006.01) |
| A61P 21/00 | (2006.01) |

(52) U.S. Cl.
USPC .............. 424/239.1; 424/185.1; 530/350

(58) Field of Classification Search .............. None
See application file for complete search history.

(56) References Cited

U.S. PATENT DOCUMENTS

| 5,846,929 A | 12/1998 | Johnson et al. |
| 2003/0009025 A1 | 1/2003 | Smith et al. |
| 2007/0166332 A1 | 7/2007 | Steward et al. |

FOREIGN PATENT DOCUMENTS

| WO | 00/61192 A2 | 10/2000 |
| WO | 2006017715 A2 | 2/2006 |

OTHER PUBLICATIONS 16 pages of an PCT communication dated Aug. 6, 2010 in the corresponding PCT/US2010/03318 application.
Carter et al., "Independent Evolution of Neurotoxin and Flagellar Genetic Loci in Proteolytic Clostridium Botulinum" 2009 BMC Genomics 10:115.
Fach et al., "Development of Real-Time PCR Tests for Detecting Botulinum Neurotoxins A, B, E, F, Producing . . . " 2009 Journal of Applied Microbiology 107:465-473.
Chaddock et al., "Expression and Purification of Catalytically Active, Non-Toxic Endopeptidase Derivatives of Clostridium Botulinum Toxin Type A" 2002 Protein Expresson and Purification 25:219-228.
Jankovic et al., "Response and Immunoresistance to Botulinum Toxin Injections" 1995 Neurology 1743-1746.
Turton et al., "Botulinum and Tetanus Neurotoxins: Structure, Function, and Therapeutic Utility" 2002 Trends in Biochemical Sciences 27(11):552-558.
Dover et al., "Novel Clostridium Botulinum Toxin Gene Arrangement With Subtype A5 and Partial Subtype B3 Botulinum Neurotoxin Genes" 2009 Journal of Clinical Microbiology 47(7):2349-2350.

*Primary Examiner* — Robert A Zeman
(74) *Attorney, Agent, or Firm* — Quarles & Brady, LLP

(57) ABSTRACT

A novel subtype of type A botulinum neurotoxin (BoNT/A) is disclosed in the application. Methods to purify the neurotoxin as well as uses thereof are also disclosed.

3 Claims, 23 Drawing Sheets

```
                                    90 ┌ BoNT/A5-A661222
                               100 ┤
                                    └ BoNT/A5-IBCA94-0216
                       100
                                      BoNT/A5-H04402 065
                                      BoNT/A1
                                      BoNT/A4
                                      BoNT/A2
                       99
                                      BoNT/A3
```
0.06  0.05  0.04  0.03  0.02  0.01  0.00

B.

```
                                    75 ┌ A5-HC-A661222
                               100 ┤
                                    └ A5-HC-IBCA94-0216
                       100
                                      A5-HC-H04402 065
                                      A1-HC
                                      A4-HC
                                      A2-HC
                       100
                                      A3-HC
```
0.06  0.05  0.04  0.03  0.02  0.01  0.00

BoNT/A5 →
HC →              — 62kD
                  — 48kD
LC →

Fig. 9

SEQ ID NO:1
atgccatttgttaataaacaatttaattataaagatcctgtaaatggtgttgatattgcttatataaaaattccaaatgcaggacaaatgcaaccagt
aaaagcttttaaaattcataataaaatatgggttattccagaaagagatacctttacaaaccctgaagaaggagatttaaatccaccaccagaag
caaaacaagttccagtttcatattatgattcaacatatttaagtacagataatgaaaaagataattatttaaagggagttacaaaattatttgagaga
atttattcaactgagcttggaagaatgttgttaacatcaatagtaaggggaataccatttgggtggaagtacaatagatacagaattaaaagtt
attgatactaattgtattaatgtgatacaaccagatggtagttatagatcagaagaacttaatctagtaataataggaccctcagctgatattataca
gtttgaatgtaaaagctttggacatgacgttttgaatcttacgcgaaatggttatggctctactcaatacattagatttagcccagatttttacatttgg
ttttgaggagtcacttgaagttgatacaaatcctctttaggtgcaggcaaatttgctacagatccagcagtaacattagcacatgaacttatacat
gctggacatagattatatggaatagcaattaatccaaataggttttaaagtaaatactaatgcctattatgaaatgagtgggttagaagtaagct
ttgaggaacttagaacatttggggaacatgatgcaaagtttatagatagtttacaggaaaacgaatttcgtctatattattataataagtttaaagat
atagcaagtacacttaataaagctaaatcaatagtaggtactactgcttcattacagtatatgaaaaatgttttaaagagaaatatctcctatctga
agatacatctggaaaattttcggtagataaattaaatttgataagttatacaaaatgttaacagagatttacacagaggataattttgttaagtttttt
aaagtacttaacagaaaacatatttgaattttgataaagccgtatttaagataaatatagtacctgaggtaaattacacaatatatgatggatttaa
tttaagaaatacaaatttagcagcaaactttaatggtcaaaatacagaaattaataatatgaattttactaaactaaaaaaattttactggattgtttga
attttataagttgctatgtgtaagagggataataacttctaaaactaaatcattagatgaaggatacaataaggcattaaatgatttatgtatcaaag
ttaataattgggacttgttctttagtccttcagaagataatttactaatgatctaaataaaggagaagaaattacatctgatactaatatagaagca
gcagaagaaaatattagtttagatttaatacaacaatattatttaaccttttaattttgataatgaacctgaaaatatttcaatagaaaatctttcaagtg
acattataggccaattagaacttatgcctaatatagaaagatttcctaatgaaaaaagtatgagttagataaatatactatgttccattatcttcgt
gctcaagaatttgaacatggtaaatctaggattgttttaacaaattctgttaacgaagcattattaaatcctagtagtgtttatacattttttcttcaga
ctatgtaaggaaagttaataaagctacggaggcagctatgtttttaggctgggtagaacaattagtatatgattttaccgatgaaactagcgaag
taagtactacggataaaattgcagatataactataattattccatatataggacctgctttaaatataggtaatatgttatataaagatgatttgtag
gtgctttaatattttcaggagctgttattctgttagaatttataccagagattgcaatacctgtattaggtacttttgcacttgtatcatatattgcgaat
aaggttctaactgttcaaacaatagataatgctttaagtaaaagaaatgaaaaatggggcgaggtctataaatatatagtaacaaattggttagc
aaaggttaatacacagattgatctaataagaaaaaaaatgaaagaagctttagaaaatcaagcagaagcaacaaaggctataataaactatca
gtataatcaatatactgaggaagagaaaaataatattaattttaatattggtgatttaagttcgaaacttaatgactctataaataaagctatgattaa
tataaataaattttttgaatcagtgctctgtttcatatttaatgaattctatgataccttatggtgttaaacggttagaagattttgatgctagtcttaaaga
tgcattattaaagtatatatatgataatagaggaactttaattggtcaagtagatagattaaaagataaagttaataatacacttagtacagatatac
cttttcagctttccaaatacgtagataatcaaagattattatctacatttactgaatatattaagaatattattaatacttctatattgaatttaagatatga
aagtaatcatttaatagacttatctaggtatgcatcagaaataaatattggtagtaaagtaaattttgatccaatagataaaaatcaaattcaattattt
aatttagaaagtagtaaaattgagataattttaaaaaatgctattgtatataatagtatgtatgaaaattttagtactagcttttggataaaaattccta
agtatttagcaagataaatctaaataatgaatatacaataataaattgtatagaaaataattcaggatggaaagtatcacttaattatggtgaaata
atctggactttgcaggataataagcaaaacatacaaagagtagtttttaaatacagtcaaatggttgctatatcagattatataaacagatggattt
ttataactatcactaataatagattaaataactctaaaatttatataaatggaagattaatagatcaaaaaccaatttcaaatttaggtaatattcatgc
tagtaataatataatgtttaaattagatggttgtagagatccacaaagatacatttggataaaatattttaatcttttcgataaagaattaaatgaaaa
agaaatcaaagatttatatgataatcaatcaaattcaggtatttaaaagacttttggggtaattatttacaatatgataaaccatactatatgttaaat
ttatatgatccaaataaatatgtcgatgtaaataatgtaggtattagagggttatatgtatcttaaagggcctagaggtagcatagtgactacaaaca
tttatttaaattcaagtttgtatatggggacaaaattattataaaaaaatatgcttctggaaataaagataatattgttagaaataatgatcgtgtatat
attaatgtagtagttaaaaataaagaatataggttagctactaatgcatcacaggcaggcgtagaaaaaatactaagtgtattagaaatacctga
tgtaggaaatctaagtcaagtagtagtaatgaagtcaaaaaatgatcaaggaataagaaataaatgcaaatgaatttacaagataataatggg
aatgatataggctttataggattccatcagtttaataatatagataaactagtagcaagtaattggtataatagacaaatagaaagatctagtagga
cttttggttgctcatgggaatttattcctgtagatgatggatggggagaaagtccactgtaa

Fig. 10

SEQ ID NO:2
MPFVNKQFNYKDPVNGVDIAYIKIPNAGQMQPVKAFKIHNKIWVIPERDTFTNPEEGDLN
PPPEAKQVPVSYYDSTYLSTDNEKDNYLKGVTKLFERIYSTELGRMLLTSIVRGIPFWGG
STIDTELKVIDTNCINVIQPDGSYRSEELNLVIIGPSADIIQFECKSFGHDVLNLTRNGY
GSTQYIRFSPDFTFGFEESLEVDTNPLLGAGKFATDPAVTLAHELIHAGHRLYGIAINPN
RVFKVNTNAYYEMSGLEVSFEELRTFGEHDAKFIDSLQENEFRLYYYNKFKDIASTLNKA
KSIVGTTASLQYMKNVFKEKYLLSEDTSGKFSVDKLKFDKLYKMLTEIYTEDNFVKFFKV
LNRKTYLNFDKAVFKINIVPEVNYTIYDGFNLRNTNLAANFNGQNTEINNMNFTKLKNFT
GLFEFYKLLCVRGIITSKTKSLDEGYNKALNDLCIKVNNWDLFFSPSEDNFTNDLNKGEE
ITSDTNIEAAEENISLDLIQQYYLTFNFDNEPENISIENLSSDIIGQLELMPNIERFPNG
KKYELDKYTMFHYLRAQEFEHGKSRIVLTNSVNEALLNPSSVYTFFSSDYVRKVNKATEA
AMFLGWVEQLVYDFTDETSEVSTTDKIADITIIIPYIGPALNIGNMLYKDDFVGALIFSG
AVILLEFIPEIAIPVLGTFALVSYIANKVLTVQTIDNALSKRNEKWGEVYKYIVTNWLAK
VNTQIDLIRKKMKEALENQAEATKAIINYQYNQYTEEEKNNINFNIGDLSSKLNDSINKA
MININKFLNQCSVSYLMNSMIPYGVKRLEDFDASLKDALLKYIYDNRGTLIGQVDRLKDK
VNNTLSTDIPFQLSKYVDNQRLLSTFTEYIKNIINTSILNLRYESNHLIDLSRYASEINI
GSKVNFDPIDKNQIQLFNLESSKIEIILKNAIVYNSMYENFSTSFWIKIPKYFSKINLNN
EYTIINCIENNSGWKVSLNYGEIIWTLQDNKQNIQRVVFKYSQMVAISDYINRWIFITIT
NNRLNNSKIYINGRLIDQKPISNLGNIHASNNIMFKLDGCRDPQRYIWIKYFNLFDKELN
EKEIKDLYDNQSNSGILKDFWGNYLQYDKPYYMLNLYDPNKYVDVNNVGIRGYMYLKGPR
GSIVTTNIYLNSSLYMGTKFIIKKYASGNKDNIVRNNDRVYINVVVKNKEYRLATNASQA
GVEKILSVLEIPDVGNLSQVVVMKSKNDQGIRNKCKMNLQDNNGNDIGFIGFHQFNNIDK
LVASNWYNRQIERSSRTFGCSWEFIPVDDGWGESPL

Fig. 11

SEQ ID NO:3 attagtaatatctatatgcaatcttatattatagttatttaattctgtaacttctactttttaatatataaattgcaccatttaataaacgtattgacttggtac
tatttaagagatttaaattttgttgtatattaattaaattatagccgtcaatagtttcagtgactctaaataaagtacctattccttggttattactagtata
aagcctaatgttagatgtatctttattattaaagttaccaggtactgtaaattcatatgaaatatagttaccaacatcaggactttgtcttgtatagtaa
tgtgcacctgttgaattaagatcatctattatattaactgaagaattcattaaatttcggagatcccccttcttctctctcgaatttatttgatttctatatt
agaagaagtttgtggtactctaatgtagtaattttatccttattaagcaaaacaactaaataacttttaacattaggactgtcaaacccagtaatata
atttattgctttaatatcatcatcacataaattcccagattggaaatttctattaccagaacctatcgcttcatatattttaatgatggtagattattctg
agcattaattttataaattcctgtagtatttactgtaaataatatataaaatggattattatttacaatacccggaatgttatatgtgtaattatctgaaat
agcagtatttattttttgtatattttcagatgggtctatgacacctactacgatttcttcctcggggccattctgtataaacccatcttcagccacttgc
gttttaactacttcagattcaggtgaaggagcattagttacttcacaatatcctaaggaaggaaggtaatactcagcttattaacaatacttccatt
ttgatagtctattaattcatactttttcataggtattataagcctttatgcatatatttttatttgaaggagcttcttctacaaatttaaataacgatgttgat
gtattaaataattgtacattgaaagcgtctttaagtcttcttcagtatattgttgtgagaattttgcatcattacttgtggtgaataatggcctagttgta
tttcttagtcgaggttgtataatacttcctgatgaacctgcttcgattaataatgtacctatcaaatctttatcatttgttcttatatatccatcaccctttat
taataacatataatccattactataaggtaatactcgttgtgtgctactaactttagaattaaaaatattgttagttggtatattttagtagtttctaaaa
tttttttatataggaattgttcatttaaaatgcacttatcattagttaaaaagtaaaaatcttatttattttttccccctggattaaattctatagacttaacat
atccaagagatggaacatataaaactgctctttctataatttcatgttgcaagactttattatttcatatctaatgtaggtatattgtaaatacatatat
aagttttattgagggagcggttttactaaattcaaatcctattggaatttgattagcttcagtaaagttagcaaatacagtttgtatattattttttatat
attcttcattgaaggatggtgttggataataatatggtatcgcattatcatttacacgtaggtccccaactattcctgttgatccattactaattacact
tccacctagtatttgattttgtctagataaatatccatccatcccctctgctaactacataattaccatcagctaaatcaatagtatcactatagtttata
acttttttcttgtatatcattataaattttttttatagatgaattcatacactttctccttttatattttttcaagtttgaacatttcatttgaattgtatatatcaaa
attaggtagtaggagtagtggttggcttaaaatattttttattagtatcataaatgtcccaggcataatctaattcattcactttatttaaacttaacataa
tataagtatttacagcgatttttaatgggaaaccagtagcatctattggataatgaatctaaagaaataaatccaaagttatcgtaacttaaatactta
tttggttctgctacattagagattttaaagcatctatttttcagccatatattctacattccattttttgattatttgcagaagattcatttgaaaatgttaatg
atcctgatacaggattttaaatataaagaatcagaaaagatagatttttatattgtaattaccattaggtagaaaagttcttttcaactgacatataaattca
cctctttataaaattagatgatagtactcatattaaattttttgttgatattaatttttatgggttacgaatataccatttctgattattatctccatgataattaa
atacttgaatatcagttccgtttgctgtttggctgttatataaatctagagctttagttttatcgcgtagattagtaattgtatatgtttcataagtatctg
gaacaggatttataagccaatattgggcatcattattttgatcattagaataaaaccctacagtattaccatttgaaaaaatccatgttagaactccg
tttgaaagtatttcattaaaaaactggtatgctgcttttcttcattatatctaattgtccatttttgattgcgatcattgttccaagtatataaattaacatt
tagatctgtcatagctacttgttgtacaactttattagaagctaatattggacttattttacatgtgaaattgttaagatctgatattatataatcttctatg
ataaattttatataatttgaattattaagtgtgctaagtttcaaattacgagctacggtatcggcatataatactaagttagggtttttataacttgcaat
aataaatgaattgttaccaatgtctttaataataaccaatattgattatctgcatttgaatcttgttgcgctgatatattatgtgttggtgcattccatgt
taaaactaaattagtattatggatattcatactttttattttataagcagcttttattagaatcatatataattctccatctttcaaggtaattctagtttgttg
aaataagctaacgttaccgttaccgtcaacttgataaaaaaataaatctgtattagccttacaggagatggtaacgattttgtcatttaatgaatttt
ggattactgaatggtgttccattatgattcctccttatttaataattaatcttacatataatatataacataatgaaattatttttttgtaaacctaaaattta
aaagcaattagtttcttttatagtaaataaagtaataatatatatattatgggggggatagcggtaaatatgaataaattgttttttacaaattaaaatgttg
aaaaatgacaacagagagtttcaagaaattttttaagcattttgaaaaaaactatagatatatttttactagaaaatataatatatatgataattacaatgat
attttgtaccatttatggtatatacttaaaaaagttgatttgagcaatttcaatacacaaaatgatttagagagatatattagtaggactttaaaagat
attgcttagatatttgcaataaaagaaagattgataagaaaataatatataattcagaaattgcagataagaaattaagcttaatagcaaatagtta
ttcaagttattcagaatttgaatttaatgatttaatatccatattacctgataatcaaaagaaaattatatatatgaaatttgttgaagatattaaggaga
tagatatagctaaaaaacttaatataagtcgtcaatctgtatataaaataaaatactggctttagagagattagaacccatattgaaaaaattaatt
aatatgtagtttatatttttaaaaattttaggttttacaaaaaatagtgtggctatgttatatataaatgataacaatatactgaaaaatatatccaaaatt
taaggggggcgtgtatagtaaataattaaaagtatgtgcgttgaaataaatttaggagagtggttagatatgaatataaatgacaacttaagtataa
attccccagtagataataaaaatgttgtagtagttagagctagaaaaactgatacgttttttaaggcttttaaggttgctcctaatatttgggtggcg
ccagagagatattatggcgaatctctgagtatagatgaagaatataaagttgatgggggaatatatgattctaattttctttcacaagatagtgaa
aaagataagttcttacaagccattattactttgttaaaaagaattaataatactaacgctggggaaaaattattatctttgatttctacagctattccat
ttccttatggatatataggtggaggatattatgcacctaatatgattacttttggatcagcaccaaaatctaataaaaaattgaattctttaatttcaag
tactattccatttccttatgcaggatatagagaaacaaattatctttcatctgaagataataaaagtttctatgcatctaatatagttattttttggtccag
gagcaaacatagtagaaaacaatactgttttttataaaaaggaagatgcagaaaatggtatgggaacaatgactgaaatatggttccaaccattt Fig. 11 (Continued)

```
ctaacctataaatatgaccaattttatattgatcctgcaatagaattaatgaaatgtttaataaaatctctttatttcttatatgggataaaaccaagtg
atgatttagttgttccatatagattaagaaatgaattagagaatatagaatactcacagttggatatagttgatttactagtatccggaggcattgat
cctaaatttataaatacagatccatattggtttatagataattatttctcaaatgcaaaaaaaatgtttgaagatcataggaatatttatgaaacagaa
attgaaggaaataatgccattggtaatgatataaaattgagattaaaacaaaagtttcgaatcaatatcaatgatatatgggaattaaatttaaatta
tttctctaaagagtttaacattatgatgccagatagatttaataatgcacttaaacattttatagaaaacaatactacaaaatagattacccagaaa
attatagtataaatggttttgttaatggtcaaattaatgctcaattatctttatcagatagaaatcaagatattataaataaacctgaagaaataattaa
tttattaaatgaaaataatgtttattaatgagaagtaatatttatggtgatggattaaaaagcactgtagatgattttacagtaattataaaatcccat
ataatagagcctatgaatatcattttaataattcaaatgattcttctttagataatgttaacattggagtaatagacaatattccagagattatagatgt
aaatccttataaggaaaattgtgataagttttcgccggtacagaaaattacaagtactagagaaattaatacaaatataccatggcctataaattat
ttacaagctcaaaataccaacaatgaaaaatttagtttatcctcagattttgtagaagtagtttcttctaaagataaatctttagtgtattctttcttatct
aatgtaatgtttatttagattccataaaggataatagtcctattgatacagataaaaaatattatttatggttaagagagattttagaaattattctttt
gatattactgcaactcaagaaattaatactaattgcggtattaataaagtagtaacttggtttggaaaagcattaaatatttaaatacatcagattct
tttgtagaagaatttcaaaatttagggccaagttcacttattaataaaaaagaaaatttaagtatgccaataattgagatttatgaaatccctaacga
tatgttaggattaccactaaatgatttaaatgaaaaattatttaacatatattctaaaaatacagcttatttaaaaaaaatctactataatttcctagatc
agtggtggacacaatattatagtcaatattttgatttaatttgtatggctaaaagatcagtgttagctcaagaaactttaataaaaagaataatacaa
aaaaaattgagttatttaataggaaattctaatatatcatctgataacttagcattgatgaatcttacaacaacaaatacattaagagatatttcaaac
gaatcacaaatagcaatgaataatgtagatagttttttaaataatgccgctatatgtgttttgaaagtaatatatatcctaaatttatttctttatggaa
caatgtattaataatataaatattaagacaaaagaatttatacaaaaatgtactaatattaatgaagatgaaaaattacaattaattaaccaaaatgtt
tttaatagcttagattttgaattcttaaacattcaaaatatgaaaagtttatttagttcagagacagcattacttataaaggaagaaacttggccttatg
aactagtgttatatgcttttcaggaatcaggtaataatgttatcggagatgcatctggtaaaaatacatcaatagaatattctaaggacataggttta
gtttatggaataaatagtgatgcattatatttaaatggatctaatcaaagtataagttttttctaatgatttctttgaaaatggattaactaatagttttca
atttattttttggttgagaaatttgggcaaagatactattaaatctaagttaataggtagtaaggaagataattgtggttgggaaatttattttcaagat
actgggttggttttaatatgatagattctaatggaaatgagaagaatatatatctatctgatgtttctaataatagttggcactatataactatatctgt
agatcgtttaaaagaacaattattaatatttattgatgataatttagtggctaatgaaagtattaaagaaattttaatatctattcaagtaatataattt
ctttattaagcgagaataatccaagttatattgagggattaactattttaaataaacccactacaagtcagaaagttttgagtaattatttaaggctc
taaataattcatatataagagacagtagtgaagaacgattagaatacaataagacatatcaattatataattatgtattttcagataagcctatatgt
gaagttaaacaaaataataatatatatttaacaattaataatacaaacaatttaaatttacaagcttctaaatttaaattattaagtatcaatccaaata
aacaatatgttcaaaaatttgatgaggtaataatatctatattagataatatggaaaaatatatagatatatctgaagataatagattgcagctaata
gacaacaaaaatagcgcaaagaagatgataattagtaatgatatatttatttctaattgtttaactctatcttgtggcggtaaatatatatgtttatcta
tgaaagatgaaaaccataattggatgatatgtaataatgatatgtcaaagtatttgtatttatggtcatttaaataattaataatttaattaatttaaata
ttataagaggtgttaaatatgccatttgttaataaacaatttaattataaagatcctgtaaatggtgttgatattgcttatataaaaattccaaatgcag
gacaaatgcaaccagtaaaagctttaaaattcataataaaatatgggttattccagaaagagataccttacaaaccctgaagaaggagattta
aatccaccaccagaagcaaaacaagttccagtttcatattatgattcaacatatttaagtacagataatgaaaaagataattatttaaagggagtt
acaaaattatttgagagaatttattcaactgagcttggaagaatgttgttaacatcaatagtaaggggaataccattttggggtggaagtacaata
gatacagaattaaaagttattgatactaattgtattaatgtgatacaaccagatggtagttatagatcagaagaacttaatctagtaataataggac
cctcagctgatattatacagtttgaatgtaaaagcttggacatgacgttttgaatcttacgcgaaatggttatggctctactcaatacattagattta
gcccagattttacatttggttttgaggagtcacttgaagttgatacaaatcctcttttaggtgcaggcaaatttgctacagatccagcagtaacatt
agcacatgaacttatacatgctggacatagattatatggaatagcaattaatccaaataggggttttaaagtaaatactaatgcctatatgaaatg
agtgggttagaagtaagctttgaggaacttagaacatttggggaacatgatgcaaagtttatagatagtttacaggaaaacgaatttcgtctatat
tattataataagtttaaagatatagcaagtacacttaataaagctaaatcaatagtaggtactactgcttcattacagtatatgaaaaatgttttaaa
gagaaatatctcctatctgaagatacatctggaaaattttcggtagataaattaaaatttgataagttatacaaaatgttaacagagatttacacag
aggataatttgttaagtttttaaagtacttaacagaaaaacatatttgaattttgataaagccgtatttaagataaatatagtacctgaggtaaatta
cacaatatatgatggatttaatttaagaaatacaaatttagcagcaaacttaatggtcaaaatacagaaattaataatatgaatttactaaactaa
aaaattttactggattgtttgaattttataagttgctatgtgtaagagggataataacttctaaaactaaatcattagatgaaggatacaataaggca
ttaaatgatttatgtatcaaagttaataattgggacttgttcttagtccttcagaagataattttactaatgatctaaataaaggagaagaaattacat
ctgatactaatatagaagcagcagaagaaaatattagtttagatttaatacaacaatattatttaacctttaattttgataatgaacctgaaaatatttc
aatagaaaatctttcaagtgacattataggccaattagaacttatgcctaatatagaaagatttcctaatggaaaaaagtatgagttagataaatat
actatgttccattatcttcgtgctcaagaatttgaacatggtaaatctaggattgtttaacaaattctgttaacgaagcattattaaatcctagtagtg
tttatacatttttttcttcagactatgtaaggaaagttaataaagctacggaggcagctatgttttaggctgggtagaacaattagtatatgattttac
```

Fig. 11 (Continued)

cgatgaaactagcgaagtaagtactacggataaaattgcagatataactataattattccatatataggacctgctttaaatataggtaatatgttat
ataaagatgattttgtaggtgctttaatattttcaggagctgttattctgttagaatttataccagagattgcaatacctgtattaggtactttttgcactt
gtatcatatattgcgaataaggttctaactgttcaaacaatagataatgctttaagtaaaagaaatgaaaaatggggcgaggtctataaatatata
gtaacaaattggttagcaaaggttaatacacagattgatctaataagaaaaaaaatgaaagaagctttagaaaatcaagcagaagcaacaaag
gctataataaactatcagtataatcaatatactgaggaagagaaaaataatattaattttaatattggtgatttaagttcgaaacttaatgactctata
aataaagctatgattaatataaataaattttttgaatcagtgctctgtttcatatttaatgaattctatgataccttatggtgttaaacggttagaagatttt
gatgctagtcttaaagatgcattattaaagtatatatatgataatagaggaactttaattggtcaagtagatagattaaaagataaagttaataatac
acttagtacagatataccttttcagctttccaaatacgtagataatcaaagattattatctacatttactgaatatattaagaatatattaatacttctat
attgaatttaagatatgaaagtaatcatttaatagacttatctaggtatgcatcagaaataaatattggtagtaaagtaaattttgatccaatagataa
aaatcaaattcaattatttaatttagaaagtagtaaaattgagataattttaaaaaatgctattgtatataatagtatgtatgaaaattttagtactagct
tttggataaaaattcctaagtattttagcaagatataatctaaataatgaatatacaataataaattgtatagaaaataattcaggatggaaagtatca
cttaattatggtgaaataatctggactttgcaggataataagcaaaacatacaaagagtagttttttaaatacagtcaaatggttgctatatcagatt
atataaacagatggatttttataactatcactaataatagattaaataactctaaaatttatataaatggaagattaatagatcaaaaaccaatttcaa
atttaggtaatattcatgctagtaataatataatgtttaaattagatggttgtagagatccacacaaagatacatttggataaaatattttaatctttttcgat
aaagaattaaatgaaaaagaaatcaaagatttatatgataatcaatcaaattcaggtatttttaaaagactttttgggtaattattacaatatgataa
accatactatatgttaaatttatatgatccaaatgaaatatgtcgatgtaaataatgtaggtattagaggttatatgtatcttaaagggcctagaggta
gcatagtgactacaaacatttatttaaattcaagtttgtatatggggacaaaatttattataaaaaaatatgcttctggaaataaagataatattgtta
gaaataatgatcgtgtatatattaatgtagtagttaaaaataaagaatataggttagctactaatgcatcacaggcaggcgtagaaaaaaatacta
agtgtattagaaatacctgatgtaggaaatctaagtcaagtagtagtaatgaagtcaaaaaatgatcaaggaataagaaataaatgcaaaatga
atttacaagataataatgggaatgatataggctttataggattccatcagtttaataatatagataaactagtagcaagtaattggtataatagaca
aatagaaagatctagtaggactttttggttgctcatgggaatttattcctgtagatgatggatggggagaaagtccactgtaattaatctcaaacta
catgagtctgtcaagaattttgtgtaaacatccataaaaattttaaa

Fig. 12

SEQ ID NO:4

```
atgaattcat ctataaaaaa aatttataat gatatacaag aaaaagttat aaactatagt
gatactattg atttagctga tggtaattat gtagttagca gaggggatgg atggatatta
tctagacaaa atcaaatact aggtggaagt gtaattagta atggatcaac aggaatagtt
ggggacctac gtgtaaatga taatgcgata ccatattatt atccaacacc atccttcaat
gaagaatata taaaaaataa tatacaaact gtatttgcta actttactga agctaatcaa
attccaatag gatttgaatt tagtaaaacc gctccctcaa ataaaaactt atatatgtat
ttacaatata cctacattag atatgaaata ataaaagtct tgcaacatga aattatagaa
agagcagttt tatatgttcc atctcttgga tatgttaagt ctatagaatt taatccaggg
gaaaaaataa ataaagattt ttacttttta actaatgata agtgcatttt aaatgaacaa
ttcctatata aaaaaatttt agaaactact aaaaatatac caactaacaa tatttttaat
tctaaagtta gtagcacaca acgagtatta ccttatagta atggattata tgttattaat
aagggtgatg gatatataag aacaaatgat aaagatttga taggtacatt attaatcgaa
gcaggttcat caggaagtat tatacaacct cgactaagaa atacaactag gccattattc
accacaagta atgatgcaaa attctcacaa caatatactg aagaaagact aaagacgct
ttcaatgtac aattatttaa tacatcaaca tcgttattta aatttgtaga agaagctcct
tcaaataaaa atatatgcat aaaggcttat aatacctatg aaaagtatga attaatagac
tatcaaaatg gaagtattgt taataaagct gagtattacc ttccttcctt aggatattgt
gaagtaacta atgctccttc acctgaatct gaagtagtta aaacgcaagt ggctgaagat
gggtttatac agaatggccc cgaggaagaa atcgtagtag gtgtcataga cccatctgaa
aatatacaaa aaataaatac tgctatttca gataattaca catataacat tccgggtatt
gtaaataata atccatttta tatattattt acagtaaata ctacaggaat ttataaaatt
aatgctcaga ataatctacc atcattaaaa atatatgaag cgataggttc tggtaataga
aatttccaat ctgggaattt atgtgatgat gatattaaag caataaatta tattactggg
tttgacagtc ctaatgttaa aagttattta gttgttttgc ttaataagga taaaaattac
tacattagag taccacaaac ttcttctaat atagaaaatc aaataaaatt cgagagagaa
gaagggatc tccgaaattt aatgaattct tcagttaata taatagtga tcttaattca
acaggtgcac attactatac aagacaaagt cctgatgttg gtaactatat ttcatatgaa
tttacagtac ctggtaactt taataataaa gatacatcta acattaggct ttatactagt
aataaccaag gaataggtac tttatttaga gtcactgaaa ctattgacgg ctataattta
attaatatac aacaaatttt aaatctctta aatagtacca agtcaatacg tttattaaat
ggtgcaattt atatattaaa agtagaagtt acagaattaa ataactataa tataagattg
catatagata ttactaat
```

Fig. 13

SEQ ID NO:5

```
MNSSIKKIYN DIQEKVINYS DTIDLADGNY VVSRGDGWIL SRQNQILGGS VISNGSTGIV
GDLRVNDNAI PYYYPTPSFN EEYIKNNIQT VFANFTEANQ IPIGFEFSKT APSNKNLYMY
LQYTYIRYEI IKVLQHEIIE RAVLYVPSLG YVKSIEFNPG EKINKDFYFL TNDKCILNEQ
FLYKKILETT KNIPTNNIFN SKVSSTQRVL PYSNGLYVIN KGDGYIRTND KDLIGTLLIE
AGSSGSIIQP RLRNTTRPLF TTSNDAKFSQ QYTEERLKDA FNVQLFNTST SLFKFVEEAP
SNKNICIKAY NTYEKYELID YQNGSIVNKA EYYLPSLGYC EVTNAPSPES EVVKTQVAED
GFIQNGPEEE IVVGVIDPSE NIQKINTAIS DNYTYNIPGI VNNNPFYILF TVNTTGIYKI
NAQNNLPSLK IYEAIGSGNR NFQSGNLCDD DIKAINYITG FDSPNVKSYL VVLLNKDKNY
YIRVPQTSSN IENQIKFERE EGDLRNLMNS SVNIIDDLNS TGAHYYTRQS PDVGNYISYE
FTVPGNFNNK DTSNIRLYTS NNQGIGTLFR VTETIDGYNL INIQQNLNLL NSTKSIRLLN
GAIYILKVEV TELNNYNIRL HIDITN
```

Fig. 14

SEQ ID NO:6

```
atgtcagttg aaagaacttt tctacctaat ggtaattaca atataaaatc tatcttttct
gattctttat atttaaatcc tgtatcagga tcattaacat tttcaaatga atcttctgca
aataatcaaa aatggaatgt agaatatatg gctgaaaata gatgctttaa aatctctaat
gtagcagaac caaataagta tttaagttac gataactttg gatttatttc tttagattca
ttatccaata gatgctactg gtttcccatt aaaatcgctg taaatactta tattatgtta
agtttaaata aagtgaatga attagattat gcctgggaca tttatgatac taataaaaat
attttaagcc aaccactact cctactacct aattttgata tatacaattc aaatgaaatg
ttcaaacttg aaaaaata
```

Fig. 15

SEQ ID NO:7

```
MSVERTFLPN GNYNIKSIFS DSLYLNPVSG SLTFSNESSA NNQKWNVEYM AENRCFKISN
VAEPNKYLSY DNFGFISLDS LSNRCYWFPI KIAVNTYIML SLNKVNELDY AWDIYDTNKN
ILSQPLLLLP NFDIYNSNEM FKLEKI
```

Fig. 16

SEQ ID NO:8

```
atggaacacc attcagtaat ccaaaattca ttaaatgaca aaatcgttac catctcctgt
aaggctaata cagatttatt ttttatcaa gttgacggta acggtaacgt tagcttattt
caacaaacta gaaattacct tgaaagatgg agaattatat atgattctaa taaagctgct
tataaaataa aaagtatgaa tatccataat actaatttag ttttaacatg gaatgcacca
acacataata tatcagcgca acaagattca aatgcagata atcaatattg gttattatta
aaagacattg gtaacaattc atttattatt gcaagttata aaaaccctaa cttagtatta
tatgccgata ccgtagctcg taatttgaaa cttagcacac ttaataattc aaattatata
aaatttatca tagaagatta tataatatca gatcttaaca atttcacatg taaaataagt
ccaatattag cttctaataa agttgtacaa caagtagcta tgacagatct aaatgttaat
ttatatactt ggaacaatga tcgcaatcaa aaatggacaa ttagatataa tgaagaaaaa
gcagcatacc agttttttaa tgaaatactt tcaaacggag ttctaacatg gatttttca
aatggtaata ctgtaaggg ttattctaat gatcaaaata atgatgccca atattggctt
ataaatcctg ttccagatac ttatgaaaca tatacaatta ctaatctacg cgataaaact
aaagctctag atttatataa cagccaaaca gcaaacggaa ctgatattca agtatttaat
tatcatggag ataataatca gaaatggtat attcgtaacc ca
```

Fig. 17

SEQ ID NO:9

```
MEHHSVIQNS LNDKIVTISC KANTDLFFYQ VDGNGNVSLF QQTRNYLERW RIIYDSNKAA
YKIKSMNIHN TNLVLTWNAP THNISAQQDS NADNQYWLLL KDIGNNSFII ASYKNPNLVL
YADTVARNLK LSTLNNSNYI KFIIEDYIIS DLNNFTCKIS PILASNKVVQ QVAMTDLNVN
LYTWNNDRNQ KWTIRYNEEK AAYQFFNEIL SNGVLTWIFS NGNTVRVYSN DQNNDAQYWL
INPVPDTYET YTITNLRDKT KALDLYNSQT ANGTDIQVFN YHGDNNQKWY IRNP
```

Fig. 18

SEQ ID NO:10

```
atgaataaat tgtttttaca aattaaaatg ttgaaaaatg acaacagaga gtttcaagaa
atttttaagc attttgaaaa aactatagat atatttacta gaaaatataa tatatatgat
aattacaatg atattttgta ccatttatgg tatatactta aaaaagttga tttgagcaat
ttcaatacac aaaatgattt agagagatat attagtagga ctttaaaaag atattgctta
gatatttgca ataaaagaaa gattgataag aaaataatat ataattcaga aattgcagat
aagaaattaa gcttaatagc aaatagttat tcaagttatt cagaatttga atttaatgat
ttaatatcca tattacctga taatcaaaag aaaattatat atatgaaatt tgttgaagat
attaaggaga tagatatagc taaaaaactt aatataagtc gtcaatctgt atataaaaat
aaaatactgg ctttagagag attagaaccc atattgaaaa aattaattaa tatg
```

Fig. 19

SEQ ID NO:11

```
MNKLFLQIKM LKNDNREFQE IFKHFEKTID IFTRKYNIYD NYNDILYHLW YILKKVDLSN
FNTQNDLERY ISRTLKRYCL DICNKRKIDK KIIYNSEIAD KKLSLIANSY SSYSEFEFND
LISILPDNQK KIIYMKFVED IKEIDIAKKL NISRQSVYKN KILALERLEP ILKKLINM
```

Fig. 20

SEQ ID NO:12

```
atgaatataa atgacaactt aagtataaat tccccagtag ataataaaaa tgttgtagta
gttagagcta gaaaaactga tacgttttt aaggcttta aggttgctcc taatatttgg
gtgcgccag agagatatta tggcgaatct ctgagtatag atgaagaata taaagttgat
gggggaatat atgattctaa ttttctttca caagatagtg aaaaagataa gttcttacaa
gccattatta ctttgttaaa aagaattaat aatactaacg ctggggaaaa attattatct
ttgatttcta cagctattcc atttccttat ggatatatag gtggaggata ttatgcacct
aatatgatta cttttggatc agcaccaaaa tctaataaaa aattgaattc tttaatttca
agtactattc catttcctta tgcaggatat agagaaacaa attatctttc atctgaagat
aataaaagtt tctatgcatc taatatagtt attttggtc caggagcaaa catagtagaa
aacaatactg ttttttataa aaggaagat gcagaaaatg gtatgggaac aatgactgaa
atatggttcc aaccatttct aacctataaa tatgaccaat tttatattga tcctgcaata
gaattaatga aatgtttaat aaaatctctt tatttcttat atgggataaa accaagtgat
gattagttg ttccatatag attaagaaat gaattagaga atatagaata ctcacagttg
gatatagttg atttactagt atccggaggc attgatccta aatttataaa tacagatcca
tattggttta tagataatta tttctcaaat gcaaaaaaaa tgtttgaaga tcataggaat
atttatgaaa cagaaattga aggaaataat gccattggta atgatataaa attgagatta
aaacaaagt ttcgaatcaa tatcaatgat atatgggaat taaatttaaa ttatttctct
aaagagttta acattatgat gccagataga tttaataatg cacttaaaca ttttatagaa
aaacaatact acaaaataga ttacccagaa aattatagta taaatggttt tgttaatggt
caaattaatg ctcaattatc tttatcagat agaaatcaag atattataaa taaacctgaa
gaaataatta atttattaaa tgaaaataat gttttattaa tgagaagtaa tatttatggt
gatggattaa aaagcactgt agatgatttt tacagtaatt ataaaatccc atataataga
gcctatgaat atcattttaa taattcaaat gattcttctt tagataatgt taacattgga
gtaatagaca atattccaga gattatagat gtaaatcctt ataaggaaaa ttgtgataag
ttttcgccgg tacagaaaat tacaagtact agagaaatta atacaaatat accatggcct
ataaattatt tacaagctca aaataccaac aatgaaaaat ttagtttatc ctcagatttt
gtagaagtag tttcttctaa agataaatct ttagtgtatt ctttcttatc taatgtaatg
ttttatttag attccataaa ggataatagt cctattgata cagataaaaa atattattta
tggttaagag agatttttag aaattattct tttgatatta ctgcaactca agaaattaat
actaattgcg gtattaataa agtagtaact tggtttggaa aagcattaaa tatttaaat
acatcagatt cttttgtaga agaatttcaa aatttagggc caagttcact tattaataaa
aaagaaaatt taagtatgcc aataattgag atttatgaaa tccctaacga tatgttagga
ttaccactaa atgatttaaa tgaaaaatta tttaacatat attctaaaaa tacagcttat
tttaaaaaaa tctactataa tttcctagat cagtggtgga cacaatatta tagtcaatat
tttgatttaa tttgtatggc taaagatca gtgttagctc aagaaacttt aataaaaaga
ataatacaaa aaaaattgag ttatttaata ggaaattcta atatatcatc tgataactta
gcattgatga atcttacaac aacaaataca ttaagagata tttcaaacga atcacaaata
gcaatgaata atgtagatag ttttttaaat aatgccgcta tatgtgtttt tgaaagtaat
atatatccta aatttatttc ttttatggaa caatgtatta ataatataaa tattaagaca
aaagaattta tacaaaaatg tactaatatt aatgaagatg aaaaattaca attaattaac
caaaatgttt ttaatagctt agattttgaa ttcttaaaca ttcaaaatat gaaagtttta
tttagttcag agacagcatt acttataaag gaagaaactt ggccttatga actagtgtta
tatgcttttc aggaatcagg taataatgtt atcggagatg catctggtaa aaatacatca
atagaatatt ctaaggacat aggtttagtt tatggaataa atagtgatgc attatattta
aatggatcta atcaaagtat aagttttct aatgatttct ttgaaaatgg attaactaat
agttttcaa tttattttg gttgagaaat ttgggcaaag atactattaa atctaagtta
ataggtagta aggaagataa ttgtggttgg gaatttatt ttcaagatac tgggttggtt
tttaatatga tagattctaa tggaaatgag aagaatatat atctatctga tgtttctaat
aatagttggc actatataac tatatctgta gatcgtttaa aagaacaatt attaatattt
attgatgata atttagtggc taatgaaagt attaaagaaa ttttaaatat ctattcaagt
aatataattt ctttattaag cgagaataat ccaagttata ttgagggatt aactatttta
aataaaccca ctacaagtca gaaagttttg agtaattatt ttaaggctct aaataattca
tataaagag acagtagtga agaacgatta gaatacaata agacatatca attatataat
tatgtatttt cagataagcc tatatgtgaa gttaaacaaa ataataatat atatttaaca
attaataata caaacaattt aaatttacaa gcttctaaat ttaaattatt aagtatcaat
ccaaataaac aatatgttca aaaatttgat gaggtaataa tatctatatt agataatatg
gaaaaatata tagatatatc tgaagataat agattgcagc taatagacaa caaaaatagc
gcaaagaaga tgataattag taatgatata tttatttcta attgtttaac tctatcttgt
ggcggtaaat atatatgttt atctatgaaa gatgaaaacc ataattggat gatatgtaat
aatgatatgt caaagtattt gtatttatgg tcatttaaa
```

Fig. 21

SEQ ID NO:13

```
MNINDNLSIN SPVDNKNVVV VRARKTDTFF KAFKVAPNIW VAPERYYGES LSIDEEYKVD
GGIYDSNFLS QDSEKDKFLQ AIITLLKRIN NTNAGEKLLS LISTAIPFPY GYIGGGYYAP
NMITFGSAPK SNKKLNSLIS STIPFPYAGY RETNYLSSED NKSFYASNIV IFGPGANIVE
NNTVFYKKED AENGMGTMTE IWFQPFLTYK YDQFYIDPAI ELMKCLIKSL YFLYGIKPSD
DLVVPYRLRN ELENIEYSQL DIVDLLVSGG IDPKFINTDP YWFIDNYFSN AKKMFEDHRN
IYETEIEGNN AIGNDIKLRL KQKFRININD IWELNLNYFS KEFNIMMPDR FNNALKHFYR
KQYYKIDYPE NYSINGFVNG QINAQLSLSD RNQDIINKPE EIINLLNENN VLLMRSNIYG
DGLKSTVDDF YSNYKIPYNR AYEYHFNNSN DSSLDNVNIG VIDNIPEIID VNPYKENCDK
FSPVQKITST REINTNIPWP INYLQAQNTN NEKFSLSSDF VEVVSSKDKS LVYSFLSNVM
FYLDSIKDNS PIDTDKKYYL WLREIFRNYS FDITATQEIN TNCGINKVVT WFGKALNILN
TSDSFVEEFQ NLGPSSLINK KENLSMPIIE IYEIPNDMLG LPLNDLNEKL FNIYSKNTAY
FKKIYYNFLD QWWTQYYSQY FDLICMAKRS VLAQETLIKR IIQKKLSYLI GNSNISSDNL
ALMNLTTTNT LRDISNESQI AMNNVDSFLN NAAICVFESN IYPKFISFME QCINNINIKT
KEFIQKCTNI NEDEKLQLIN QNVFNSLDFE FLNIQNMKSL FSSETALLIK EETWPYELVL
YAFQESGNNV IGDASGKNTS IEYSKDIGLV YGINSDALYL NGSNQSISFS NDFFENGLTN
SFSIYFWLRN LGKDTIKSKL IGSKEDNCGW EIYFQDTGLV FNMIDSNGNE KNIYLSDVSN
NSWHYITISV DRLKEQLLIF IDDNLVANES IKEILNIYSS NIISLLSENN PSYIEGLTIL
NKPTTSQKVL SNYFKALNNS YIRDSSEERL EYNKTYQLYN YVFSDKPICE VKQNNNIYLT
INNTNNLNLQ ASKFKLLSIN PNKQYVQKFD EVIISILDNM EKYIDISEDN RLQLIDNKNS
AKKMIISNDI FISNCLTLSC GGKYICLSMK DENHNWMICN NDMSKYLYLW SFK
```

SUBTYPE OF *CLOSTERIDIUM BOTULINUM* NEUROTOXIN TYPE A AND USES THEREOF

CROSS-REFERENCE TO RELATED APPLICATION

This application claims priority from U.S. provisional patent application Ser. No. 61/174,331 filed Apr. 30, 2009, which is incorporated by reference herein.

STATEMENT REGARDING FEDERALLY SPONSORED RESEARCH OR DEVELOPMENT

This invention was made with United States government support awarded by the following agencies: NIH AI065359. The United States has certain rights in this invention.

BACKGROUND OF THE INVENTION

Neurotoxigenic strains of *Clostridium butyricum* and *Clostridium baratii* produce botulinum neurotoxins (BoNTs), which are the most potent neurotoxins known. BoNTs are characterized as Category A Select Agents and are considered potential bioterrorism threats (Arnon, S. S. et al. 2001, Jama 285:1059-1070).

BoNT is synthesized as a single chain polypeptide (molecular weight of 150 kDa) with relatively little toxic potency. It becomes toxic upon cleavage by trypsin or bacterial enzymes into a heavy chain (100 kDa) and a light chain (50 kDa). Three dimensional structure shows that BoNTs contain a receptor-binding domain located in the C-terminal region of the heavy chain, a catalytic domain (the light chain) with endopeptidase activity on neuronal substrates and a translocation domain located in the N-terminal region of the heavy chain.

BoNTs can be immunologically distinguished using homologous antitoxins into seven serotypes, designated A-G. Different serotypes of BoNTs have regions of homology, particularly in the residues defining the catalytic active site, in the translocation domain, and in the two cysteine residues forming the disulfide bond connecting the heavy chain and the light chain. The least degree of homology is in the carboxyl region of the heavy chain, which is involved in neurospecific binding. Indeed, among these serotype distinctions there is considerable genetic variation, as demonstrated by the recognition of at least 24 subtypes (Carter, A. T., et al., 2009, BMC Genomics 10:115; Dover, N., et al., 2009, J. Clin. Microbiol. 47:2349-2350; Hill, K. K. et al. 2007, J. Bacteriol 189:818-832; Smith, T. J. et al. 2005, Infect. Immun. 73:5450-5457). These subtypes have been distinguished based on their degree of genetic variation with subtypes having a minimum of 2.6% divergence on the amino acid level (Webb, R. P., et al., 2009, Vaccine 27:4490-4497). These subtypes can also be distinguished by mouse bioassay, as a new subtype is resistant to neutralization by antibodies raised against known subtypes.

Despite of the variations, different serotypes of BoNTs act through a similar mechanism: by inhibiting the release of acetylcholine, a neurotransmitter, from the presynaptic nerve terminal and thus causing local chemodenervation. The action of BoNTs involves a four step process: (1) high affinity, serotype specific binding by the heavy chains to receptors on presynaptic membrane of cholinergic nerve endings; (2) receptor mediated, energy dependent internalization of the complex; (3) translocation from the acidic endosome to the cytosol; and (4) enzymatic cleavage, by the light chain, of specific proteins that are critical for fusion of the presynaptic acetylcholine vesicle with the presynaptic membrane, thus preventing release of acetylcholine into the synapse.

BoNT/A is of particular importance and interest since it is the most significant threat in bioterrorism and has been increasingly used as a pharmaceutical modality (Aoki, K. R. 2003, Clin. Dermatol. 21:476-480; Delgado, M. R. 2003, J. Am. Acad. Orthop. Surg. 11:291-294). Thus far, four distinct subtypes of BoNT type A, i.e., BoNT/A1, BoNT/A2, BoNT/A3 and BoNT/A4, have been identified in this manner (Arndt, J. W. et al. 2006, J. Mol. Biol. 362:733-742; Smith, T. J. et al. 2007, PLoS ONE 2:e1271).

The success of BoNTs as a therapeutic derives from certain important attributes of the toxin: (a) exceptionally specific binding to the presynaptic membrane of cholinergic terminals; (b) extremely high potency; (c) remarkable specificity for catalytic cleavage of proteins involved in neurotransmitter trafficking and exocytosis; (d) minimal spread from the injection site; (e) limited and mild adverse effects, and (f) extraordinary long duration of action. Table 1 summarizes the clinical applications of BoNTs.

Although each injection of BoNT has a long duration of effective action, repeated injection is necessary at about three month intervals because although the affected nerve terminals are no longer capable of neurotransmitter exocytosis, newly formed sprouts do release acetylcholine and form a functional synapse. As a result, after about three months, the original terminal resumes exocytosis and the sprouts regress to return the neuromuscular junction to its original state.

TABLE 1

| Clinical applications of botulinum toxin |
|---|
| Dystonia |
| Blepharospasm and lid apraxia<br>Oromandibular-facial-lingual dystonia<br>Cervical dystonia (torticollis)<br>Laryngeal dystonia (spasmodic dysphonia)<br>Limb dystonia<br>Task specific dystonia (eg, writer's or other occupational cramps)<br>Other focal/segmental dystonias (primary, secondary)<br>Other involuntary movements |
| Hemifacial spasm<br>Limb, head, voice, chin tremor<br>Palatal myoclonus<br>Motor and phonic tics (including coprolalia)<br>Nystagmus and oscillopsia<br>Myokymia<br>Inappropriate muscle contractions |
| Spasticity (stroke, cerebral palsy, head injury, multiple sclerosis)<br>Painful rigidity<br>Strabismus<br>Bruxism and temporo-mandibular joint syndrome<br>Stuttering<br>Chronic tension (muscle contraction) headaches<br>Lumbosacral strain and back spasms<br>Radiculopathy with secondary muscle spasm<br>Myofascial pain syndromes<br>Achalasia (lower oesophageal sphincter spasm)<br>Spasm of the inferior constrictor of the pharynx<br>Spasm of the sphincter of Oddi<br>Spastic bladder, detrusor sphincter dyssynergia<br>Anismus<br>Vaginismus<br>Other applications |
| Protective ptosis<br>Hyperlachrymation<br>Drooling (sialorrhoea)<br>Hyperhidrosis<br>Gustatory sweating<br>Anal fissure |

TABLE 1-continued

Clinical applications of botulinum toxin

Constipation
Obesity (distal stomach)
Cosmetic (wrinkles, brow furrows, frown lines, "crow's feet", platysma lines, facial asymmetry)
Tennis elbow and other sports injuries A growing impediment in BoNT administration is the development in patients of antibodies that react with and neutralize the toxin, thereby eliminating the effectiveness of the toxin for medicinal and cosmetic purposes. As a result, some patients become unresponsive to subsequent repeated treatments. Studies have shown that the heavy chain of the protein, used for substrate binding, is the primary portion against which humans develop antibodies against BoNT/A1, the predominat form of botulinum toxin used clinically.

The observation that BoNTs are chimeric molecules comprised of distinct protein domains suggests that designed chimeric neurotoxin could be constructed with enhanced or distinct therapeutic utility.

Needed in the art are novel subtypes of BoNTs which are not easily neutralized by existing antibodies in patients and thus possess distinct therapeutic utility, as well as novel subtypes of BoNTs which cause no or less development of antibodies in patients.

SUMMARY OF THE INVENTION

We disclose here the identification, purficiation and characterization of a novel isoform of *Clostridium botulinum* type A botulinum neurotoxin (BoNT/A), BoNAT/A5, in *Clostridium botulinum* strain A661222.

In one embodiment, the present invention is an isolated nucleotide encoding BoNT/A5. Preferably, the nucleotide sequence is SEQ ID NO:1.

In another embodiment, the present invention is a substantially purified BoNT/A5 protein. Preferably, the protein is encoded by the nucleotide comprising SEQ ID NO:1. More preferably, the protein is at least 90% pure. Most preferably, the protein is at least 95% pure.

In another embodiment, the present invention is a method of purifying BoNT/A5 complex comprising the steps of inoculating appropriate *C. botulinum* strain culture capable of producing BoNT/A5 complex, subjecting the *C. botulinum* culture to acid precipitation, and isolating BoNT/A5 complex by chromatography. Preferably, the chromatography is at pH5.5 using a DEAE-Sephadex A-50 column. Preferably, the method further comprises the step of separation of a 150 kDa toxin from complexing proteins by anion exchange chromatography and a final purification of the 150 kDa toxin by cation exchange chromatography.

In yet another embodiment, the present invention is a BoNT/A5 complex purified by the method described above.

In another embodiment, the present invention is a method of obtaining an antibody specific to BoNT/A5. In one embodiment, the method comprises the steps of obtaining purified BoNT/A5 either in its complete form or its separate domain parts, inactivating the purified BoNT/A5, administering the inactivated BoNT/A5 to a mammalian host in a standard process and obtaining an antibody. Preferably, the inactivation of the purified BoNT/A5 is via heating the purified BoNT/A5 or via formaldehyde treatment.

In one preferred embodiment, the antibody is a monoclonal antibody. Preferably, the monoclonal antibody is obtained via the method described above, wherein the monoclonal antibody is obtained via generating hybridomas from the fusion of spleen cells, which are from the mammalian host administered with the inactivated BoNT/A5, with myeloma cells from the same mammalian species and harvesting monoclonal antibodies from the hybridomas. Preferably, the mammalian host is a mouse.

In another preferred embodiment, the antibody is a polyclonal antibody. Preferably, the polyclonal antibody is obtained via the method described above, wherein the administration of inactivated BoNT/A5 to the mammalian host is followed by booster injections to increase antibody yield against inherent epitopes, collecting serum from the mammalian host, and purifying antibody specific to BoNT/A5 by affinity chromatography. Preferably, the method further comprises the step of testing the purified antibody for specificity to BoNT/A5.

In one embodiment, the present invention is an antibody obtained by the method described above.

In another embodiment, the present invention is a method of treating a patient in need of botulinum toxin therapy comprising the step of supplying substantially purified BoNT/A5 complex or neurotoxin to the patient.

In yet another embodiment, the present invention is a method of improving the medicinal use of BoNTs, comprising the step of substituting BoNT/A5 for BoNT/A1 for patients refractive to treatment with BoNT/A1.

Other embodiments, features and advantages of the present invention will become apparent on review of the specification, claims and drawings.

BRIEF DESCRIPTION OF THE DRAWINGS

FIG. 1 A-B show graphical representations of degree of relatedness among the amino acid sequences of the BoNT/A1-5 subtypes. Panel A shows comparison of the entire BoNT among all 5 *C. botulinum* type A subtypes. Panel B shows comparison of the heavy chain of toxins of all 5 *C. botulinum* type A subtypes. A1 is from the ATCC 3502 strain, A2 is from the Kyoto F strain, A3 from the CDC/A3 strain, A4 from the 657Ba strain and the BoNT/A5 sequence was derived from the strain listed in the figure.

FIG. 8 shows coomassie blue stained SDS-PAGE gel of purified BoNT/A5 under reducing and non-reducing condition. NR: non-reducing, R: reducing, M: Marker, HC: heavy chain, LC: light chain.

FIG. 9 shows nucleotide sequence encoding BoNAT/A5 from *Clostridium Botulinum* strain A661222.

FIG. 10 shows amino acid sequence of BoNT/A5 from *Clostridium Botulinum* strain A661222.

FIG. 11 shows genomic DNA sequence of BoNT/A5 neurotoxin cluster with HA genes from *Clostridium Botulinum* strain A661222.

FIG. 12 shows nucleotide sequence encoding HA70 from *Clostridium Botulinum* strain A661222.

FIG. 13 shows amino acid sequence of HA70 from *Clostridium Botulinum* strain A661222.

FIG. 14 shows nucleotide sequence encoding HA17 from *Clostridium Botulinum* strain A661222.

FIG. 15 shows amino acid sequence of HA17 from *Clostridium Botulinum* strain A661222.

FIG. 16 shows nucleotide sequence encoding HA33 from *Clostridium Botulinum* strain A661222.

FIG. 17 shows amino acid sequence of HA33 from *Clostridium Botulinum* strain A661222.

FIG. 18 shows nucleotide sequence encoding botR from *Clostridium Botulinum* strain A661222.

FIG. 19 shows amino acid sequence of botR from *Clostridium Botulinum* strain A661222.

FIG. 20 shows nucleotide sequence encoding NTNH from *Clostridium Botulinum* strain A661222.

FIG. 21 shows amino acid sequence of NTNH from *Clostridium Botulinum* strain A661222.

DESCRIPTION OF THE INVENTION

In General

Figure 2:
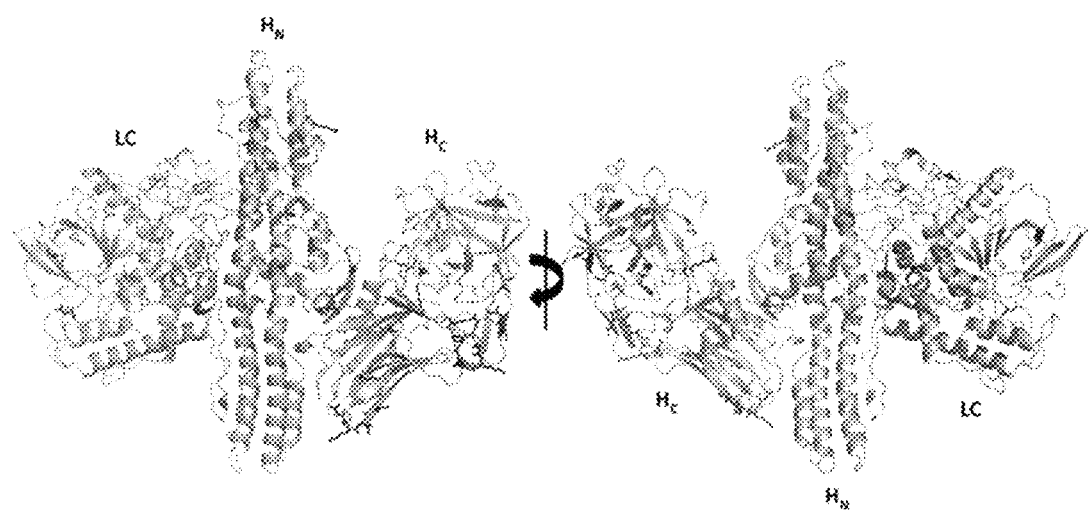
FIG. 2 shows 3D model of the new BoNT/A5 subtype. The varied residues are shown as sticks with black color. Overall structure is displayed as ribbon diagram with a grey Cα.

The present invention relates to a novel subtype of type A botulinum neurotoxin (BoNT/A) and provides methods to purify the neurotoxin as well as uses thereof.

During the past few years, scientists have engaged in the identification and study of novel *C. botulinum* BoNT/A subtypes. A new subtype of BoNT/A was identified and named BoNT/A5 with five strains containing the neurotoxin (Carter, A. T., et al., 2009, BMC Genomics 10:115; Dover, N., et al., 2009, J. Clin. Microbiol. 47:2349-2350). Among these five strains, four have neurotoxin sequences that are identical and the fifth is 99.8% identical to the others on the amino acid level. The subtype features both a high degree of similarity to BoNT/A1 and a HA type gene cluster which is present in only BoNT/A1 clusters and none of the other BoNT/A subtypes. The Johnson laboratory identified one of the A5 strains, a strain of *C. botulinum*, A661222 (Jacobson, M. J. et al. 2008, Microbiology. 154(Pt 8):2408-2415, and U.S. provisional patent application 61/174,331, both of which are incorporated by reference herein).

The identification of A661222 is described in detail in Jacobson, M. J. et al. 2008. Briefly, a broad range of BoNT/A-producing bacteria were analyzed using Multi Locus Sequence Typing (MLST) followed by sequencing the bont/a and its associated neurotoxin cluster genes in strains demonstrating a unique MLST ST profile. The A661222 strain demonstrated a ST profile which placed it similar to the reference strain (ATCC 3502) but still retained significant divergence from the reference strain in a manner similar to strains known to possess a unique BoNT/A subtype. This led to the belief that the A661222 strain might possess a novel BoNT/A subtype.

Indeed, as described below in the Examples, we discovered a novel form of the *C. botulinum* encoded type A botulinum neurotoxin (BoNT/A) and identified it in the A661222 strain. Briefly, the neurotoxin gene and its associated genes were completely sequenced and analyzed on both the nucleotide and amino acid level. Thirty six amino acid differences were observed between BoNT/A1 and BoNT/A5, with most of the differences in the heavy chain. (Table 2, below, summarizes the changes.) 3-D molecular modeling was performed comparing this form of BoNT/A5 with the established BoNT/A1 subtype. These modeling studies on BoNT/A focused on determining if amino acid differences observed in BoNT/A5 would have an affect on known antibody epitope sites. The BoNT/A5 protein was then purified from culture and its toxicity was determined. The ability of BoNT/A1 specific antibodies to neutralize BoNT/A5 was also tested by mouse bioassay.

BoNT/A5 offers the advantages of possessing unique epitopes in the heavy chain, which are likely to affect the ability of antibodies capable of neutralizing BoNT/A1 to neutralize BoNT/A5. Thus, it may have significant advantages over existing commercial botulinum toxins used medicinally, particularly for patients that have immunity to BoNT/A1, which is a major limitation of current technology.

In one embodiment, the present invention is a substantially purified nucleotide sequence encoding BoNT/A5. Preferably, the sequence is SEQ ID NO:1 or substantially identical to SEQ ID NO:1, preferably 99% identical.

In another embodiment, the present invention is a substantially purified BoNT/A5 protein comprising SEQ ID NO:2, preferably at a purity rate of at least 95%, preferably encoded by the nucleotide sequence comprising SEQ ID NO: 1 or a nucleotide sequence substantially identical to SEQ ID NO:1.

In another embodiment, the present invention is a method of purifying BoNT/A5 complex and toxin. A preferable method comprises inoculating a starting culture with A661222 overnight and then using that culture to inoculate a carboy of media. Acid precipitation of a 96 hour culture would then be performed. Extraction of crude toxin complex from acid precipitate would then be performed. Toxin complex would be isolated from crude extract by chromatography at pH 5.5 using a DEAE-Sephadex A-50 column. 150 kDa toxin would typically be separated from complexing proteins by anion exchange chromatography on a DEAE-Sephadex A-50 column at pH 7.9. The final purification of the 150 kDa toxin would typically be via cation exchange chromatography on a SP sephadex column at pH 7.0.

In another embodiment, the present invention is a method of using the substantially purified BoNT/A5 complex. In one embodiment, a prophetic method comprises supplying BoNT/A5 to a patient in need of botulinum toxin therapy (refering to Table 1). Given that the complex is quite similar to the BoNT/A1 complex, BoNT/A5 is likely to be used as an alternative to BoNT/A1 for medicinal and cosmetic purposes but is likely to exert effects faster than BoNT/A1. Typically, one would use less than 100 $LD_{50}$ of BoNT/A5 in one treatment.

In another embodiment, the present invention is a method of improving the medicinal use of BoNTs, comprising the steps of substituting BoNT/A5 for another BoNT/A subtype.

It is also envisioned that the present invention is a method of obtaining an antibody specific to BoNT/A5. Methods of producing antibodies is well known in the art. One could obtain either monoclonal or polyclonal antibodies specific to BoNT/A5. Typically, one would obtain purified BoNT/A5 either in its complete form or its separate domain parts, inactivate the purified BoNT/A5, administer the inactivated BoNT/A5 to a mammalian host in a standard process and obtain an antibody.

If monoclonal antibodies are needed, one would typically generate hybridomas by fusing spleen cells, which are from the mammalian host administered with the inactivated BoNT/

A5, with myeloma cells from the same mammalian species and harvest monoclonal antibodies from the hybridomas. One would typically use mice as the mammalian host, although other mammals, such as rabbits, can also be used.

If polyclonal antibodies are needed, one would typically increase antibody yield against inherent epitopes by administering booster injections to the mammalian host receiving the inactivated BoNT/A5. One would then collect serum from the mammalian host and purify antibody specific to BoNT/A5 by affinity chromatography. Preferably, one would test the purified antibody for specificity to BoNT/A5. The knowledge to select a mammalian host to produce polyclonal antibodies is well known in the art. Mammals can be used as mammalian host include rabbits, mice, chickens, goats, guinea pigs, hamsters, horses rats, sheep and donkeys. Preferably, rabbits are used.

In one embodiment, the present invention is an antibody obtained by the method described above.

The present invention has been described above with respect to its preferred embodiments. Other forms of this concept are also intended to be within the scope of the claims.

EXAMPLES

Example 1

Results
Identification and Sequencing of the Neurotoxin Gene and its Associated Cluster Genes PCR and sequencing reactions were performed on the neurotoxin and the associated neurotoxin cluster genes of *C. botulinum* A661222, and the results were compiled using the VectorNTI Suite Program. These studies involved a process of amplifying overlapping pieces of the neurotoxin and its associated cluster. Based on this work, it was determined that the A661222 strain contained only one neurotoxin gene cluster consisting of a complete HA cluster with ha70, ha17, ha33, botR, ntnh and bont/a. This arrangement is consistent with the cluster arrangement identified in other BoNT/A5 producing strains (Carter, A. T., et al., 2009, BMC Genomics 10:115; Dover, N., et al., 2009, J. Clin. Microbiol. 47:2349-2350).

Comparison of the Neurotoxin and Associated HA Cluster Proteins Between Strain A661222 and Two Other A5 Strains IBCA94-0216 and H04402 065

When the neurotoxin gene cluster of strain A661222 was compared to that of the A5 strains IBCA94-0216 and H04402 065, it was observed that the neurotoxin cluster genes and neurotoxin gene from A661222 strain were identical to those from the IBCA94-0216 strain (Dover, N., et al., 2009, J. Clin. Microbiol. 47:2349-2350). But there was 1% difference between A661222 strain and H04402 065 strain (Carter, A. T., et al., 2009, BMC Genomics 10:115) for all the genes except the ha17 and botR genes which were identical on the nucleotide level. On the amino acid level, the neurotoxin protein for the two strains was 99.8% similar and identical. HA70 was 99.2% similar and identical and HA33 was 99.7% similar and identical between the two strains. The NTNH proteins of the two strains were 99.9% similar and identical. Sequence comparisons of the BoNT/As demonstrated the high degree of homology among the BoNT/A5 strains as they grouped together and were clearly separated from the other Type A subtypes for both the entire length of the protein and the heavy chain portion (FIGS. 1A and 1B).

Comparison of the Neurotoxin and Associated HA Cluster Proteins Between Strain A661222 and the *C. botulinum* A1 Strain ATCC 3502

Analysis of the bont/a gene sequences of *C. botulinum* strains A661222 and the A1 strain ATCC 3502 demonstrated significant homology with the amino acid sequences having 97.1% and 97.9% identity and similarity respectively. There were only thirty-six amino acid differences between the two strains and the differences are mainly located in the heavy chain of the toxin, which were spread between the translocation domain and the binding domain (FIG. 2). Only four differences were located in the light chain (LC) (Table 2). This high degree of homology made it possible to generate a model for the BoNT/A5 subtype based on already known BoNT/A structures (Lacy, D. B., et al., 1998, Nat. Struct. Biol. 5:898-902; Stenmark, P., et al., 2008, PLoS Pathog. 2008, 4(8):e1000129).

The HA cluster genes demonstrated high homology between ATCC 3502 and A661222 (Table 3). The ha70 genes were 98% identical on the nucleotide level and 97.4% similar and 97.3% identical on the amino acid level. The ha17 gene was 97.7% identical on the nucleotide level and 97.3% similar and identical on the amino acid level. Also, the botR gene was 98.3% identical on the nucleotide level between the two strains and 97.2% similar and 96.6% identical on the amino acid level. The ntnh gene was 98.4% identical between the two strains and was 98.2% and 97.8% similar and identical on the amino acid level respectively. The ha33 gene demonstrated 95.0% nucleotide identity between the two strains, but only 91.5% similarity and 90.5% identity on the amino acid level.

TABLE 2

Designation of the thirty-six amino acid differences found between BoNT/A1 and BoNT/A5.

| LC | HCN | HCC | |
|---|---|---|---|
| D102E | A567V | K897E | N1006A |
| E171D | R581S | V926I | V1017I |
| G268E | K592R | R948K | T1063P |
| K381E | D707G | N954S | H1064Q |
| | D767G | S955K | D1103N |
| | E775D | S957N | V1143I |
| | | M968I | M1144V |
| | | T990N | R1156M |
| | | Q991K | A1208V |
| | | E992Q | T1232R |
| | | I993N | A1259D |
| | | K994I | L1278F |
| | | I1005V | R1294S |

The comparison was performed using the sequence of the BoNT/A1 and the first amino
acid written is from the sequence of that subtype. Light Chain (LC) comprises the amino
acid from #1 to #437, Heavy Chain N-terminal (HCN) comprises the amino acid from
438 to #872 and Heavy Chain C-terminal (HCC) comprises the amino acid from #873 to #1296.

TABLE 3

| Genes | ha70 | ha33 | ha17 | botR | ntnh | bont/a |
|---|---|---|---|---|---|---|
| Nucleotide | 98.0 | 95.0 | 97.7 | 98.3 | 98.4 | 98.6 |
| Amino acid | 97.4/97.3 | 91.5/90.5 | 97.3/97.3 | 97.2/96.6 | 98.2/97.8 | 97.9/97.1 |

Comparison of the bont/a and its associated cluster genes between C. botulinum strains A661222 and ATCC 3502 on both the nucleotide and amino acid levels. Nucleotide values are the % of identity, amino acid values are the % of similarity/identity respectively.

The sequence alignment between all the A subtypes has shown that the new A5 subtype is diverse compared to A3 and A4, somewhat close to A2, but is most similar to A1. The different domains of the toxin were compared and all the results show that the C-terminal part of the heavy chain is the most conserved domain through all subtypes (Table 4). This makes sense given the need to conserve areas of interaction between the protein receptor and ganglioside.

TABLE 4

| | Holo-toxin | LC 1-437 | HC 438-1296 | HCN 438-872 | HCC-N 873-1093 | HCC-C 1094-1296 |
|---|---|---|---|---|---|---|
| BoNT/A1 | 97 | 99 | 96 | 98 | 92 | 96 |
| BoNT/A2 | 90 | 95 | 88 | 87 | 87 | 92 |
| BoNT/A3 | 85 | 81 | 87 | 85 | 87 | 91 |
| BoNT/A4 | 87 | 89 | 87 | 86 | 80 | 94 |

Comparison between BoNT/A5 and the other BoNT/A subtypes. The toxin was split in several domains and subdomains to determine the % of identity between the subtypes. LC: Light Chain, HC: Heavy Chain, HCN: Heavy Chain N-terminal, HCC-N: Heavy Chain C-terminal N-portion, HCC-C: Heavy Chain C-terminal C-portion.

Antibody Recognition

Figure 3:
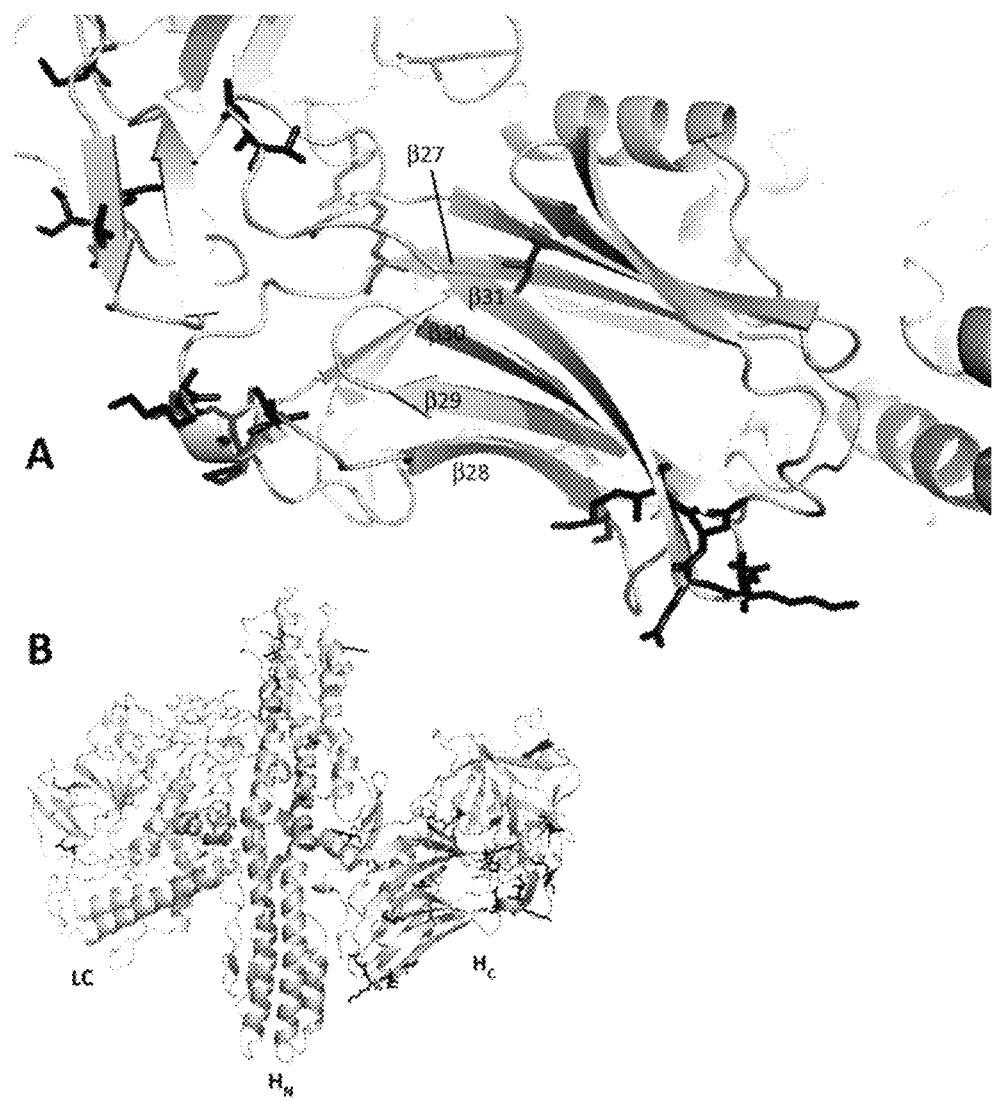
FIG. 3 is ribbon diagrams of the important epitopes area. (A) The varied residues are shown as sticks with black color. (B) This view localizes the area in the overall structure of the protein.

An epitope comparison was done utilizing certain specific peptides of the A2 HC domain based on previous work. Although the identity between the A5 and A2 sequences for the overall HC domain were low, the specific identity for those peptide regions is around 98% between the A5 and A2 subtypes compared to only 83% between the A5 and A1 subtypes. Four different regions in the HC of the protein were selected (Table 5). These peptides are known to be important for antibody recognition since they were characterized as highly sensitive epitopes (Atassi, M. Z., et al., 2004, Protein J. 23:39-52, Dolimbek, B. Z., et al., 2007, Mol. Immunol. 44:1029-1041, Garcia-Rodriguez, C., et al., 2007, Nat. Biotechnol. 25:107-116, Lacy, D. B., et al., 1999, J. Mol. Biol. 291:1091-1104, Smith, T. J., et al., 2005, Infect. Immun. 73:5450-5457, Zarebski, L. M., et al., 2008, Expert Rev. Vaccines 7:55-74). The antibodies generated against A1 could be significantly affected by the differences in these regions even though the identity of the entire amino acid chains of A1 and A5 is close to 97%. Previous works have shown that the differences observed in A2 in this region are sufficient to disturb the binding of the antibodies (Garcia-Rodriguez, C., et al., 2007, Nat. Biotechnol. 25:107-116, Smith, T. J., et al., 2005, Infect. Immun. 73:5450-5457). 40% of the differences observed in BoNT/A5 compared to BoNT/A1 were found in these important areas (FIG. 3).

TABLE 5

Comparison of specific peptides of BoNT/A1, A2 and A5 that are known to be targets for antibody neutralization.

| | A1 vs A2 | A5 vs A1 | A5 vs A2 |
|---|---|---|---|
| 925-957 | 88 | 85 | 97 |
| 967-1013 | 85 | 83 | 98 |
| 1051-1069 | 79 | 90 | 85 |
| 1275-1296 | 86 | 91 | 96 |

All numbers are the percentage of identity between the specific subtypes analyzed.

Figure 4:
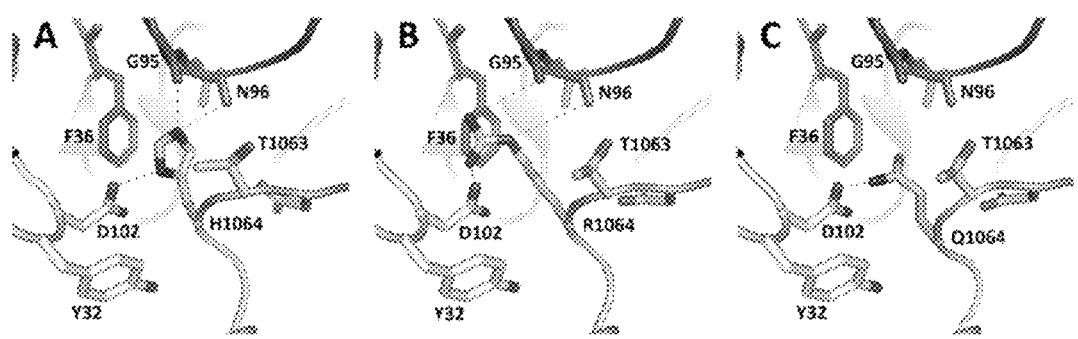
FIG. 4 shows close-up view of sequence variability between H1064 of BoNT/A1 (A), modeled R1064 of BoNT/A2 (B) and Q1064 of BoNT/A5 (C) in complex with CR1 ($V_L$ in dark grey and positioned at the upper part of each panel, and $V_H$ in light grey and positioned at the lower left part of each panel). BoNT/A1, BoNT/A2 and BoNT/A5 are showed at the lower right part of each panel.

Garcia-Rodriguez et al. have shown that several amino acids are important to optimize the interactions between certain antibodies and BoNT/A1 (Garcia-Rodriguez, C., et al., 2007, Nat. Biotechnol. 25:107-116). Some of these are different in BoNT/A5 making it similar to BoNT/A2, but several residues are also conserved (Table 6). The amino acids are listed according to their importance in the interactions between the BoNT/A1 and the two Fab species, AR2 and CR1. The different $K_D$ values were measured and proposed to affect the importance of these residues for antibody affinity. The most significant amino acid was H1064 which is deeply buried in the interface between the Fab and the toxin (FIG. 4A). The truncation of the side chain of H1064 to alanine reduces the affinity of AR2 and CR1 for BoNT/A1 by more than 200,000 fold (Garcia-Rodriguez, C., et al., 2007, Nat. Biotechnol. 25:107-116). The introduction of a mutated H1064R into the BoNT/A1 HC reduced the affinity for AR2 and CR1 by only 41- and 188-fold. This decrease is less profound probably due to the fact that the arginine can interact with the Fab amino acids as the modeling shows (FIG. 4B) (Garcia-Rodriguez, C., et al., 2007, Nat. Biotechnol. 25:107-116). In BoNT/A5, the difference is more pronounced because the H1064 is substituted for a glutamine, which is not able to pi-stack with F36. Furthermore, Q1064 has just one positive charge to interact with D102 and thus the stability of that loop decreases at the complex interface (FIG. 4C). The affinity would be lower compared to the mutated arginine form. That indicates that the antibodies developed against that BoNT/A1 area would be expected to have difficulty interacting with A5 and being able to neutralize it.

TABLE 6

Amino acids that are known to optimize antibody binding with BoNT/A.

| BoNT/A1 | BoNT/A2 | BoNT/A5 |
|---|---|---|
| Ser 902 | Asp | Ser |
| Phe 917 | Ile | Phe |
| Asn 918 | Asn | Asn |
| Leu 919 | Leu | Leu |
| Glu 920 | Glu | Glu |
| Phe 953 | Phe | Phe |
| Asn 954 | Ser | Ser |
| Ser 955 | Lys | Lys |
| Ile 956 | Ile | Ile |
| Lys 1056 | Lys | Lys |
| Asp 1058 | Asp | Asp |

TABLE 6-continued

Amino acids that are known to optimize
antibody binding with BoNT/A.

| BoNT/A1   | BoNT/A2 | BoNT/A5 |
|-----------|---------|---------|
| Arg 1061  | Arg     | Arg     |
| Asp 1062  | Asp     | Asp     |
| Thr 1063  | Pro | Pro |
| His 1064  | Arg | Gln |
| Arg 1065  | Arg     | Arg     |
| Gly 1292  | Gly     | Gly     |
| Arg 1294  | Ser | Ser |

The five BoNT/A1 amino acids that differ in BoNT/A5 and have direct contact with CR1 are in bold (Dineen, S. S., et al., 2003, Curr. Microbiol. 46: 345-352).

SNAP-25 Interaction

Figure 5:
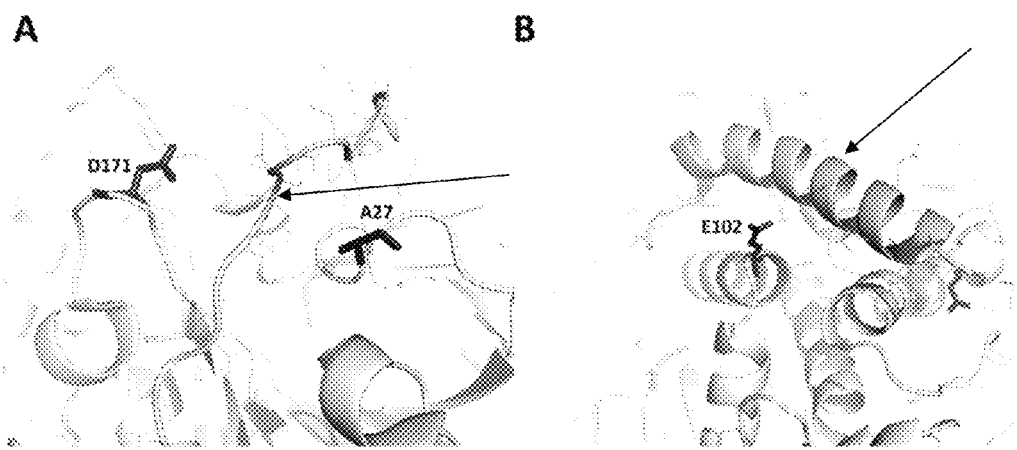
FIG. 5 is a representation of BoNT/A5 LC in complex with SNAP-25 (arrows). The three mutated amino acids in BoNT/A5 versus BoNT/A1 are shown as sticks with black color. SNAP-25 is the stick pointed out by the arrow in panel A and the Cα pointed out by the arrow in panel B.

The LC structure of the BoNT/A5 was superimposed over the BoNT/A1 LC structure in complex with the SNAP25 (pdb code 1xTG) (Breidenbach, M. A., et al., 2004, Nature 432: 925-929). The amino acids involved in the recognition of the peptide are mostly the same except for three of them. In A5 D102 was mutated to glutamic acid, E171 was transformed to aspartic acid (FIG. 5A) and V27 to alanine (FIG. 5B). The side chains are the same in term of charge and hydrophobicity but not in term of length. The impact on the specificity and the selectivity of the target should be weak.

Active Site

Figure 6:
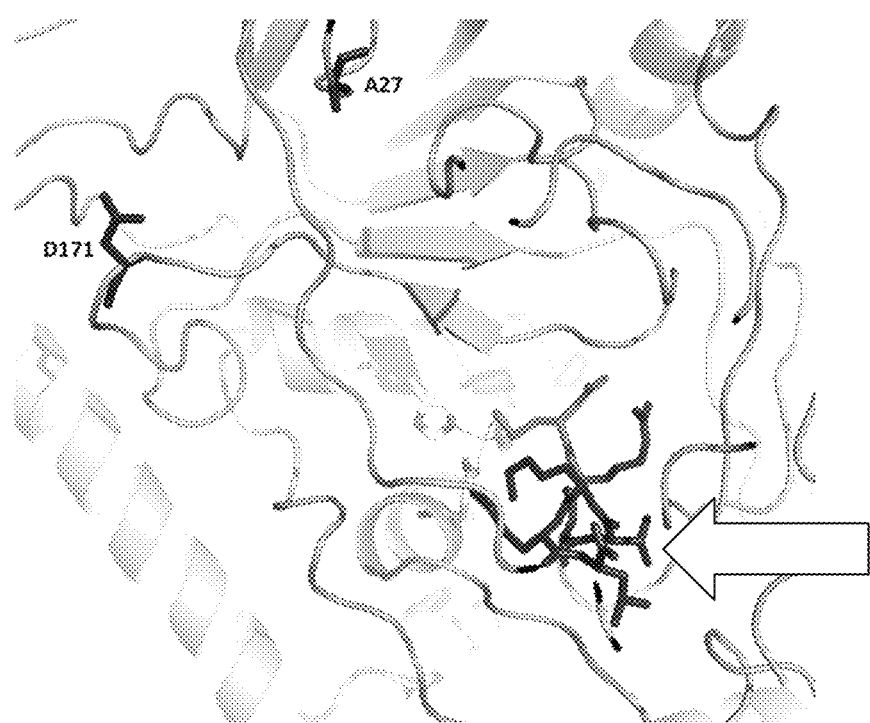
FIG. 6 is a view of the BoNT/A5 active site in complex with the N-Ac-CRATKML (black sticks pointed out by the block arrow) and the two closer mutated amino acids (A27 and D171) are shown as sticks with black color.

All catalytic residues in the active site are conserved in the new A5 subtype. The amino acids described as to perform hydrogen bonds with the substrate are the same in A5 (Silvaggi, N. R., et al., 2008, Biochemistry 47:5736-5745). Likewise, the different pockets involved in the substrate binding are conserved (S1, S1', S2', S3', S4' and S5'). The closest mutation is distant from the active site (FIG. 6).

The Ganglioside Binding Site of BoNT/A5

Figure 7:
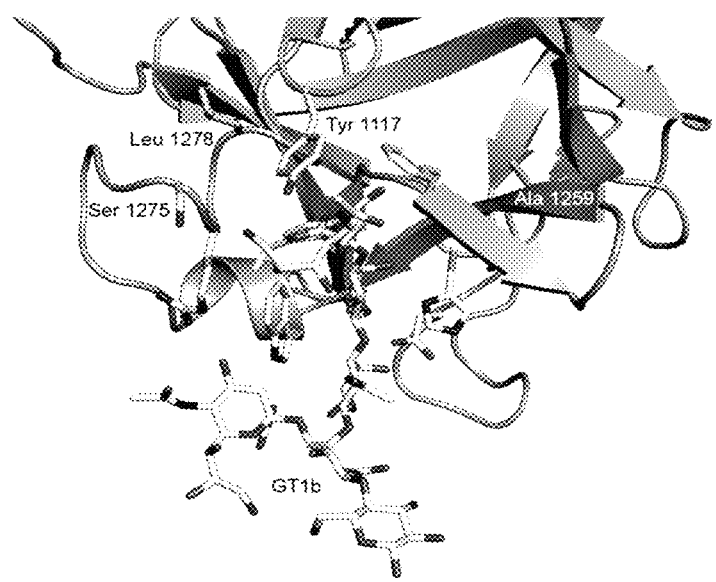
FIG. 7 shows BoNT/A1 in complex with GT1b (PDB: 2VU9). GT1b is represented as sticks. BoNT/A1 is represented as sticks with Cα. Leu 1278 and Ala 1259 that correspond to Phe 1278 and Asp 1259 in BoNT/A5 are marked out.

The structure of botulinum neurotoxin A1 in complex with the ganglioside GT1b has recently been determined (Stenmark, P., et al., 2008, PLoS Pathog. 2008, 4(8):e1000129). Amino acid alterations specific for A5 were then applied to this known structure to determine how they would affect ganglioside binding (FIG. 7). All of the amino acids that directly interact with GT1b are conserved between subtypes A1 and A5; these are Tyr 1117, Glu1203, Phe 1252, His 1253, Ser 1264, Trp 1266, Tyr 1267, Ser 1275 and Arg 1276. There are two amino acids in the second coordination sphere that are different between the two serotypes; Leu 1278 and Ala 1259 in BoNT/A1 correspond to Phe 1278 and Asp 1259 in BoNT/A5 (FIG. 7). Asp 1259 in BoNT/A5 is going to be located approximately 6 A from the ganglioside and is likely to interact with Lys 1121. This interaction is absent in BoNT/A1 and the difference will influence the electrostatics of the binding site, however, it is unlikely that this mutation will have any major effects on the ganglioside binding. In serotype B, E and the tetanus toxin the position corresponding to 1259 in BoNT/A5 is conserved as an aspartate (Rummel, A., et al., 2004, Mol. Microbiol. 51:631-643). Leu 1278 in BoNT/A1 is not conserved and is a phenylalanine in BoNT/A5; subtypes A2 and A4 also have a phenylalanine in this position (Arndt, J. W., et al., 2006, J. Mol. Biol. 362:733-742). Leu 1278 is located between Tyr 1117 and Ser 1275 in the BoNT/A1 GT1b complex; both Tyr 1117 and Ser 1275 form hydrogen bonds to SiaS of GT1b (Stenmark, P., et al., 2008, PLoS Pathog. 2008, 4(8):e1000129). The substitution of Leu 1278 (BoNT/A1) for a phenylalanine (BoNT/A5) is likely to influence the ganglioside affinity and specificity. The position of the Tyr 1117 and Ser 1275 can be changed and the position of the somewhat flexible loop harboring Ser 1275 could be affected (Lacy, D. B., et al., 1998, Nat. Struct. Biol. 5:898-902). A variety of mutations of Tyr 1117 has recently been shown to increase the affinity between the heavy chain of the toxin and nerve cells (U.S. patent publication US2007/0299008 A1), indicating that changes in this area are important for the ganglioside binding properties of the toxins.

Structural Analysis of the HA33 Protein from the BoNT/A5 Gene Cluster

HA33 is one of the major components of the progenitor toxin complex and is important for its immunogenicity and carbohydrate binding properties (Arndt, J. W., et al., 2005, J. Mol. Biol. 346:1083-1093; Sharma, S. K., et al., 2000, J. Nat. Toxins 9:357-362). The sequence identity between HA33/A1 and HA33/A5 is 90.5%; this makes it the component of the progenitor complex proteins with the least degree of conservation between A1 and A5 (Table 3). The structure of HA33/A1 has been solved and it consists of two β-trefoil fold domains (Arndt, J. W., et al., 2005, J. Mol. Biol. 346:1083-1093), with most of the sequence differences in this section located on the surface of the protein. There is a significant difference in the degree of conservation of the two domains between HA33/A5 and HA33/A1; the N-terminal domain is 93.9% identical and the C-terminal domain is 87.1% identical. This pattern of conservation has also been observed in an analysis of the sequence conservation between other serotypes (Arndt, J. W., et al., 2005, J. Mol. Biol. 346:1083-1093). The higher degree of conservation of the N-terminal domain indicates that it is mediating contacts to the rest of the progenitor toxin complex. The less conserved C-terminal domain is likely to be solvent exposed and to mediate binding to carbohydrates. The residues that have been suggested to be involve in carbohydrate binding are conserved between HA33/A1 and HA33/A5 (Arndt, J. W., et al., 2005, J. Mol. Biol. 346:1083-1093). Most of the immunogenic response of the progenitor complex has been attributed to the C-terminal part of HA33 (Sharma, S. K., et al., 2000, J. Nat. Toxins 9:357-362); the relatively high sequence variability of HA33/A5 could lead to a different immunological response of the A5 progenitor toxin complex than the A1 progenitor complex that is used extensively for medical applications.

Purification of BoNT/A5 and Determination of Toxicity

Figure 8:
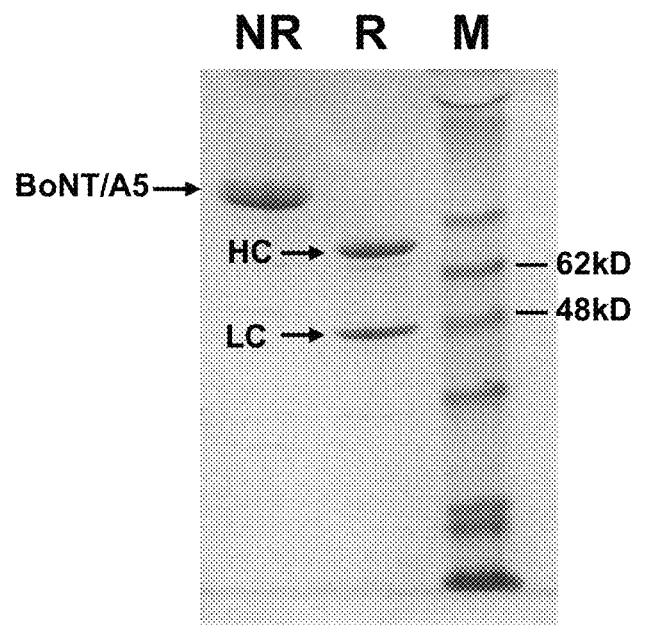

The BoNT/A5 was able to be purified by using the purification method previously used to isolate BoNT/A1. This was expected because BoNT/A5 is most closely related to BoNT/A1 among the type A subtypes and they are the only subtypes to have a HA cluster arrangement associated with the bont/a. Purified BoNT/A5 was confirmed by SDS-PAGE under reducing condition (FIG. 8) and mouse bioassay. SDS-PAGE data showed that 95% pure BoNT/A5 was obtained after the final chromatography step. Specific toxicity of 150 kDa protein was determined to be ~1.25×10$^8$ LD$_{50}$/mg.

Neutralization of BoNT/A1 and BoNT/A5 Using an anti-BoNT/A1 Antibody

To assess the effect of the variations at specific epitopes of BoNT/A5 from BoNT/A1 on antibody neutralization, it was necessary to use a mouse model with a high titer of both toxin and antibody raised against a highly immunogenic BoNT/A1 toxin. This approach was used as it would more effectively identify how epitope differences between the two toxins affect neutralization. As disclosed below, our results indicate that the differences at key epitopes between the two toxins may affect the ability of antibodies to bind to and neutralize the individual toxins.

More specifically, the neutralization results showed that 2 μl anti-BoNT/A1 antibody was able to fully neutralize 10,000 $LD_{50}$ of either BoNT/A1 or BoNT/A5, but was not able to completely neutralize 12,000 $LD_{50}$ of either toxin subtype. The data indicate that both BoNT/A1 and BoNT/A5 have very similar binding reactions with anti-BoNT/A1 antibody. However, there were some differences in the time to death of mice between the ones injected with the BoNT/A1+antibody mixture and the ones injected with the BoNT/A5+antibody mixture. The mice injected with a BoNT/A5+antibody mixture died one day faster than those injected with a BoNT/A1+antibody mixture at a 12,000 $LD_{50}$ dose. At the higher dose of 16,000 $LD_{50}$, it took mice injected with BoNT/A1+antibody mixture 2 days to die while mice injected with BoNT/A5+antibody mixture died within 4 hours, suggesting the antibodies were less effective at neutralizing BoNT/A5 compared to BoNT/A1 at dosages of 12,000 $LD_{50}$ and 16,000 $LD_{50}$. Additionally, mice injected with 10,000 $LD_{50}$ BoNT/A5+antibody mixture exhibited more severe symptoms than those injected with 10,000 $LD_{50}$ BoNT/A1+antibody even though all of the mice survived for 4 days.

Taken as a whole, the above data indicate that, although the ability of anti-BoNT/A1 antibody to bind to lower levels of BoNT/A1 and BoNT/A5 are similar, the structural differences between BoNT/A1 and BoNT/A5 are more visible when higher levels of toxins are used, which is consistent with our prediction (see paragraph [0047]).

Discussion

Prior publications have identified a novel BoNT/A subtype termed BoNT/A5. This designation was based on the level of divergence compared to known BoNT/A subtypes but did not identify the importance of these differences on a biochemical level. Our laboratory identified a strain producing this neurotoxin and analyzed it using protein modeling to assess the effect of its amino acid differences compared to BoNT/A1. There are thirty six amino acids differences between the neurotoxins of strains A661222 and ATCC 3502 (BoNT/A1) with thirty-two of them present in the heavy chain which is responsible for binding to neural cells and a target for antibody neutralization. BoNT/A5 was able to be purified by using the method previously to purify BoNT/A1. The neutralization experiment also performed to compare the binding reaction to a BoNT/A1 specific antibody between the BoNT/A1 and the BoNT/A5.

BoNT/A5 is unique compared to the other BoNT/A subtypes as it is highly similar to BoNT/A1 but also exhibits similarities to BoNT/A2 in areas that have been previously shown to affect antibody binding. The most important of these changes was at residue 1064. Previous studies have shown that mutating this residue from its original histidine to an alanine has the effect of decreasing binding by 200,000 fold as the pi-stacking between the histidine and F36 from the antibodies. In BoNT/A5, this residue is substituted for a glutamine and the pi stacking is also not present based on protein modeling experiments. This led to the hypothesis that the BoNT/A5 might have a different antibody neutralization profile than BoNT/A1.

The ability of the BoNT/A5 to form a complex with the ganglioside GT1b was also analyzed. All of the amino acids that directly interact with GT1b are conserved between subtypes A1 and A5; these are Tyr 1117, Glu 1203, Phe 1252, His 1253, Ser 1264, Trp 1266, Tyr 1267, Ser 1275 and Arg 1276. There are two amino acids in the second coordination sphere that are different between the two serotypes; Leu 1278 and Ala 1259 in BoNT/A1 correspond to Phe 1278 and Asp 1259 in BoNT/A5 (FIG. 7). Asp 1259 in BoNT/A5 is going to be located approximately 6 A from the ganglioside and is likely to interact with Lys 1121. This interaction is absent in BoNT/A1 and the difference will influence the electrostatics of the binding site, however, it is unlikely that this mutation will have any major effects on the ganglioside binding.

One of the toxin associated proteins was also analyzed via molecular modeling procedures. The amino acid sequence identity between HA33/A1 and HA33/A5 is 90.5% compared to the other genes which are highly homologous (97-98%). Some of these changes however appear to have little affect on the ability of HA33 to perform its role in the formation of a BoNT complex as the residues that have been suggested to be involve in carbohydrate binding are conserved between HA33/A1 and HA33. However, most of the immunogenic response of the progenitor complex has been attributed to the C-terminal part of HA33 which in HA33/A5 is only 87.1% identical compared to HA33/A1.

BoNT/A5 was able to be purified by using the method to purify the BoNT/A1, this was expected because of high degree of homologous between these two toxins. Both BoNT/A1 and BoNT/A5 were able to be neutralized by 2 μl anti-BoNT/A1 antibody at a dose of 1,000 LD50 but could not be completely neutralized at a dose of 12,000 LD50. The data indicated the binding between each toxin and the BoNT/A1 specific antibody was very similar but differences in the time to death of mice were observed between the two toxins. The mice injected with a BoNT/A5+antibody mixture died one day faster than those injected with a BoNT/A1+antibody mixture at a 12,000 LD50 dose. At the higher dose of 16,000 LD50, it took mice injected with the BoNT/A1+antibody mixture 2 days to die while only took mice injected with the BoNT/A5+antiboy mixture to die within 4 hours. Additionally, mice injected with 10,000 LD50 BoNT/A5+antibody mixture exhibited more severe symptoms than those injected with 10,000 LD50 BoNT/A1+antibody mixture even though all of the mice survived for 4 days. This indicates that the binding between BoNT/A1 and BoNT/A5 to anti-BoNT/A1 antibody might have slight differences which were consistent with comparative structure predictions.

An intriguing question is how this particular BoNT/A subtype arose. The strain itself is significantly different from the reference strain ATCC 3502 as it demonstrated a unique ST profile from MLST analysis implying that the strains are not closely related. While the two strains were significantly different under this analysis, they did bear some degree of similarity. Specifically, they had high degrees of similarity in most of their BoNT associated genes (between 97.7 and 98.4% identity on the nucleotide level). Only one of the genes (ha33) demonstrated significant divergence, as it was only 95% identical. This is interesting as it is located in the middle of the cluster arrangement, flanked by ha70 and ha17 on one side and botR and ntnh on the other. What makes this really interesting though is that these two flanking regions are expressed in opposite directions. Based on this, there is the possibility that the HA33 gene was so divergent between the two strains compared as it is the most likely area for a recombination event to occur at some point in the origin of the cluster. This would be in keeping with the results seen elsewhere that the complex originated from a mammalian virus, perhaps of a neurotropic source (DasGupta, B. R., 2006, J. Gen. Appl. Microbiol. 52:1-8; Johnson, E. A., et al., 2001, Toxicon 39:1703-1722). Additionally, it would explain the HA33 gene demonstrating significant sequence divergence but why few of these alterations affect the ability of the protein to engage in binding with the BoNT to help form the complex.

Example 2

Materials and Methods

Bacterial strains and growth conditions. Clostridium botulinum strains A661222 and ATCC 3502 included in this study were from the Eric A. Johnson (EAJ) strain collection. The A661222 strain was grown from a lyophilized culture which was received from the Lanzhou Institute in February 1981. Cultures were grown in 10 mL of sterile TPGY media (per liter: 50 g trypticase peptone, 5 g Bacto peptone, 4 g Δ-glucose, 20 g yeast extract, 1 g cysteine-HC1, at pH 7.4) for 2 days at 37° C. under anaerobic conditions.

Total genomic DNA isolation. Total genomic DNA was isolated from C. botulinum by lysozyme and proteinase K treatment as described previously (Dineen, S. S., et al., 2003, Curr. Microbiol. 46:345-352). DNA was then diluted to a concentration of 50 ng/μL and used for PCR amplification.

PCR amplification and DNA sequencing. PCR amplifications were performed using the GeneAmp® High Fidelity PCR System (Applied BioSystems). PCR cycles were as follows: 95° C. for 2 minutes, followed by 25 cycles of 95° C. for 1 minute, an annealing step for 45 seconds at 48° C., 72° C. for extension, followed by 1 cycle of 72° C. extension for 10 minutes. Extension time depended on the length of the fragment being amplified. Following amplification, PCR products were isolated using the PureLink™ PCR Purification Kit (Invitrogen). Sequencing was performed using conditions advised by the University of Wisconsin Biotechnology Center using the ABI PRISM® BigDye™ Cycle Sequencing Kit (Applied BioSystems). Primers used for PCR and sequencing for the HA cluster, ntnh and the bont/a gene are the same as those used before (Jacobson, M. J., et al., 2008, Appl. Environ. Microbiol. 74:2778-2786). PCRs were performed in a staggered manner such that the amplicons produced overlapping products for each of the genes in the neurotoxin cluster. Appropriate primers were then used for sequencing each PCR product. Correct assembly of the contigs was verified using overlapping sequence data with each region of the sequence being analyzed at least four times. Sequencing analysis was performed at the University of Wisconsin Biotechnology Center and final sequencing results were analyzed using the Vector NTI Suite Program (Invitrogen). Sequences for the neurotoxin cluster genes and bont/a from A661222 were determined and disclosed in FIGS. 9-21. Specifically, FIGS. 9 and 10 disclose nucleotide and amino acid sequences of BoNT/A5, respectively. FIG. 11 discloses genomic DNA sequence of BoNT/A5 neurotoxin cluster with HA genes including HA70 (reverse), HA17 (reverse), HA33 (reverse), botR (forward), NTNH (forward) and BoNT/A5 (forward). FIGS. 12 and 13 disclose nucleotide and amino acid sequences of HA70, respectively. FIGS. 14 and 15 disclose nucleotide and amino acid sequences of HA17, respectively. FIGS. 16 and 17 disclose nucleotide and amino acid sequences of HA33, respectively. FIGS. 18 and 19 disclose nucleotide and amino acid sequences of botR, respectively. FIGS. 20 and 21 disclose nucleotide and amino acid sequences of NTNH, respectively.

Sequence alignment. Amino acid sequences of BoNT/A subtypes A1-A5 were aligned using Clustal W and MEGA software to produce a UPGMA phylogeny tree of the subtypes as a whole and for their heavy chains.

Molecular modeling. The first model comparing the BoNT/A's was generated with the program Coot (Emsley, P., et al., 2004, Acta Crystallogr. D Biol. Crystallogr. 60:2126-2132) using the crystal structures of the BoNT/A1 (PDB code 1BTA) (Lacy, D. B., et al., 1998, Nat. Struct. Biol. 5:898-902). Pymol was used to generate illustrations (Delano, W. L., The PyMOL Molecular Graphics System. In Anonymous. DeLano Scientific LLC, San Carlos, Calif., USA).

Purification of BoNT/A5 and determination of toxicity. The BoNT/A5 toxin was purified using the previously described protocol used for the purification of BoNT/A1 (DasGupta, B. R., et al., 1984, Toxicon 22:415-424). The purified BoNT/A5 was visualized on a 4-12% NuPage SDS-PAGE (Invitrogen) under reducing and non-reducing condition to assess protein purity.

The specific toxicity of the purified BoNT/A5 toxin was determined by IP injection using four toxin concentrations of 15 pg, 10 pg, 6.67 pg and 4.45 pg per mouse. The toxin was diluted in 0.5 ml gel phosphate buffer and four mice were injected per each concentration and observed for 4 days for symptoms. The LD50/mg of toxin was calculated using the method described in Reed and Muench (Reed, L. J., et al., 1938, Am. J. Hyg. 27:493-497).

Neutralization of BoNT/A5 using anti-BoNT/A1 antibody. Polyclonal anti-BoNT/A1 antibody was raised in rabbit and then protein A purified. The antibody was tittered so 1 μl of this antibody can neutralize 5000 LD50 of BoNT/A1. In this study, 2 μl antibody was used to neutralize 16,000 LD50, 12,000 LD50, 10,000 LD50, 5,000 LD50, 2,500 LD50, 1,250 LD50 respectively either with BoNTA1 or BoNT/A5 to compare antibody neutralization between BoN/A1 and BoNT/A5. Toxin was diluted with gel phosphate to achieve the appropriate LD50 concentrations. The different mixtures of toxin and antibody were incubated at 37° C. for 90 minutes prior to injection. Two mice were injected with 0.5 ml of the toxin+antibody mixture respectively and were observed for 4 days for symptoms.

We claim:

1. A substantially purified BoNT/Az5 protein, wherein the protein is encoded by the nucleotide comprising SEQ ID NO:1 or by a nucleotide sequence at least 99% identical with SEQ ID NO:1.

2. The BoNT/A5 protein of claim 1, wherein the purity of the protein is at least 90%.

3. The BoNT/A5 protein of claim 1, wherein the purity of the protein is at least 95%.

* * * * *

UNITED STATES PATENT AND TRADEMARK OFFICE
CERTIFICATE OF CORRECTION

| | |
|---|---|
| PATENT NO. | : 8,440,204 B2 |
| APPLICATION NO. | : 12/769754 |
| DATED | : May 14, 2013 |
| INVENTOR(S) | : Eric A. Johnson et al. |

It is certified that error appears in the above-identified patent and that said Letters Patent is hereby corrected as shown below:

In the Specifications:

Column 1, lines 14-16, "This invention was made with United States government support awarded by the following agencies: NIH AI065359. The United States has certain rights in this invention." should be -- This invention was made with government support under AI065359 awarded by the National Institutes of Health. The government has certain rights in the invention. --

Signed and Sealed this
Ninth Day of July, 2013

Teresa Stanek Rea
*Acting Director of the United States Patent and Trademark Office*

SEQUENCE LISTING

```
<160> NUMBER OF SEQ ID NOS: 13

<210> SEQ ID NO 1
<211> LENGTH: 3891
<212> TYPE: DNA
<213> ORGANISM: Clostridium botulinum

<400> SEQUENCE: 1
atgccatttg ttaataaaca atttaattat aaagatcctg taaatggtgt tgatattgct      60
tatataaaaa ttccaaatgc aggacaaatg caaccagtaa aagctttaa aattcataat     120 aaaatatggg ttattccaga aagagatacc tttacaaacc ctgaagaagg agatttaaat     180
```

```
ccaccaccag aagcaaaaca agttccagtt tcatattatg attcaacata tttaagtaca      240
gataatgaaa aagataatta tttaaaggga gttacaaaat tatttgagag aatttattca      300
actgagcttg aagaatgtt gttaacatca atagtaaggg gaataccatt ttggggtgga      360
agtacaatag atacagaatt aaaagttatt gatactaatt gtattaatgt gatacaacca      420
gatggtagtt atagatcaga agaacttaat ctagtaataa taggaccctc agctgatatt      480
atacagtttg aatgtaaaag ctttggacat gacgttttga atcttacgcg aaatggttat      540
ggctctactc aatacattag atttagccca gattttacat ttggttttga ggagtcactt      600
gaagttgata caaatcctct tttaggtgca ggcaaatttg ctacagatcc agcagtaaca      660
ttagcacatg aacttataca tgctggacat agattatatg gaatagcaat taatccaaat      720
agggttttta aagtaaatac taatgcctat tatgaaatga gtgggttaga agtaagcttt      780
gaggaactta gaacatttgg ggaacatgat gcaaagttta tagatagttt acaggaaaac      840
gaatttcgtc tatattatta taataagttt aaagatatag caagtacact taataaagct      900
aaatcaatag taggtactac tgcttcatta cagtatatga aaaatgtttt taaagagaaa      960
tatctcctat ctgaagatac atctggaaaa ttttcggtag ataaattaaa atttgataag     1020
ttatacaaaa tgttaacaga gatttacaca gaggataatt ttgttaagtt ttttaaagta     1080
cttaacagaa aaacatatt gaattttgat aaagccgtat ttaagataaa tatagtacct     1140
gaggtaaatt acacaatata tgatggattt aatttaagaa atacaaattt agcagcaaac     1200
tttaatggtc aaaatacaga aattaataat atgaatttta ctaaactaaa aaattttact     1260
ggattgtttg aattttataa gttgctatgt gtaagaggga taataacttc taaaactaaa     1320
tcattagatg aaggatacaa taaggcatta aatgatttat gtatcaaagt taataattgg     1380
gacttgttct ttagtccttc agaagataat tttactaatg atctaaataa aggagaagaa     1440
attacatctg atactaatat agaagcagca gaagaaaata ttagtttaga tttaatacaa     1500
caatatattt taacctttaa ttttgataat gaacctgaaa atatttcaat agaaaatctt     1560
tcaagtgaca ttataggcca attagaactt atgcctaata tagaaagatt tcctaatgga     1620
aaaaagtatg agttagataa atatactatg ttccattatc ttcgtgctca agaatttgaa     1680
catggtaaat ctaggattgt tttaacaaat tctgttaacg aagcattatt aaatcctagt     1740
agtgtttata catttttttc ttcagactat gtaaggaaag ttaataaagc tacgaggca     1800 gctatgtttt taggctgggt agaacaatta gtatatgatt ttaccgatga aactagcgaa     1860
gtaagtacta cggataaaat tgcagatata actataatta ttccatatat aggacctgct     1920
ttaaatatag gtaatatgtt atataaagat gattttgtag gtgctttaat attttcagga     1980
gctgttattc tgttagaatt tataccagag attgcaatac ctgtattagg tacttttgca     2040
cttgtatcat atattgcgaa taaggttcta actgttcaaa caatagataa tgctttaagt     2100
aaaagaaatg aaaaatgggg cgaggtctat aaatatatag taacaaattg gttagcaaag     2160
gttaatacac agattgatct aataagaaaa aaaatgaaag aagctttaga aaatcaagca     2220
gaagcaacaa aggctataat aaactatcag tataatcaat atactgagga agagaaaaat     2280
aatattaatt ttaatattgg tgatttaagt tcgaaactta atgactctat aaataaagct     2340
atgattaata taaataaatt tttgaatcag tgctctgttt catatttaat gaattctatg     2400
ataccttatg gtgttaaacg gttagaagat tttgatgcta gtcttaaaga tgcattatta     2460
aagtatatat atgataatag aggaactttta attggtcaag tagatagatt aaaagataaa     2520
gttaataata cacttagtac agatatacct tttcagcttt ccaaatacgt agataatcaa     2580
```

-continued

```
agattattat ctacatttac tgaatatatt aagaatatta ttaatacttc tatattgaat   2640
ttaagatatg aaagtaatca tttaatagac ttatctaggt atgcatcaga aataaatatt   2700
ggtagtaaag taaattttga tccaatagat aaaaatcaaa ttcaattatt taatttagaa   2760
agtagtaaaa ttgagataat tttaaaaaat gctattgtat ataatagtat gtatgaaaat   2820
tttagtacta gcttttggat aaaaattcct aagtatttta gcaagataaa tctaataat    2880 gaatatacaa taataaattg tatagaaaat aattcaggat ggaaagtatc acttaattat   2940
ggtgaaataa tctggacttt gcaggataat aagcaaaaca tacaaagagt agtttttaaa   3000
tacagtcaaa tggttgctat atcagattat ataaacagat ggattttat aactatcact    3060 aataatagat taaataactc taaaatttat ataaatggaa gattaataga tcaaaaacca   3120
atttcaaatt taggtaatat tcatgctagt aataatataa tgtttaaatt agatggttgt   3180
agagatccac aaagatacat ttggataaaa tattttaatc ttttcgataa agaattaaat   3240 gaaaagaaa tcaaagattt atatgataat caatcaaatt caggtatttt aaaagacttt    3300
tggggtaatt atttacaata tgataaacca tactatatgt taaatttata tgatccaaat   3360
aaatatgtcg atgtaaataa tgtaggtatt agaggttata tgtatcttaa agggcctaga   3420
ggtagcatag tgactacaaa catttattta aattcaagtt tgtatatggg gacaaaattt   3480
attataaaaa aatatgcttc tggaaataaa gataatattg ttagaaataa tgatcgtgta   3540
tatattaatg tagtagttaa aaataaagaa tataggttag ctactaatgc atcacaggca   3600
ggcgtagaaa aaatactaag tgtattagaa atacctgatg taggaaatct aagtcaagta   3660
gtagtaatga agtcaaaaaa tgatcaagga ataagaaata aatgcaaaat gaatttacaa   3720
gataataatg ggaatgatat aggctttata ggattccatc agtttaataa tatagataaa   3780
ctagtagcaa gtaattggta taatagacaa atagaaagat ctagtaggac ttttggttgc   3840
tcatgggaat ttattcctgt agatgatgga tggggagaaa gtccactgta a           3891
```

<210> SEQ ID NO 2
<211> LENGTH: 1296
<212> TYPE: PRT
<213> ORGANISM: Clostridium botulinum
<400> SEQUENCE: 2

```
Met Pro Phe Val Asn Lys Gln Phe Asn Tyr Lys Asp Pro Val Asn Gly
 1               5                  10                  15

Val Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Glu Leu Gly Arg Met Leu Leu Thr Ser Ile Val
           100                 105                 110

Arg Gly Ile Pro Phe Trp Gly Gly Ser Thr Ile Asp Thr Glu Leu Lys
       115                 120                 125

Val Ile Asp Thr Asn Cys Ile Asn Val Ile Gln Pro Asp Gly Ser Tyr
   130                 135                 140

Arg Ser Glu Glu Leu Asn Leu Val Ile Ile Gly Pro Ser Ala Asp Ile
```

-continued

```
            145                 150                 155                 160

Ile Gln Phe Glu Cys Lys Ser Phe Gly His Asp Val Leu Asn Leu Thr
                165                 170                 175

Arg Asn Gly Tyr Gly Ser Thr Gln Tyr Ile Arg Phe Ser Pro Asp Phe
                180                 185                 190

Thr Phe Gly Phe Glu Glu Ser Leu Glu Val Asp Thr Asn Pro Leu Leu
                195                 200                 205

Gly Ala Gly Lys Phe Ala Thr Asp Pro Ala Val Thr Leu Ala His Glu
            210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Glu His Asp Ala Lys
                260                 265                 270

Phe Ile Asp Ser Leu Gln Glu Asn Glu Phe Arg Leu Tyr Tyr Tyr Asn
                275                 280                 285

Lys Phe Lys Asp Ile Ala Ser Thr Leu Asn Lys Ala Lys Ser Ile Val
            290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                325                 330                 335

Lys Phe Asp Lys Leu Tyr Lys Met Leu Thr Glu Ile Tyr Thr Glu Asp
                340                 345                 350

Asn Phe Val Lys Phe Phe Lys Val Leu Asn Arg Lys Thr Tyr Leu Asn
                355                 360                 365

Phe Asp Lys Ala Val Phe Lys Ile Asn Ile Val Pro Glu Val Asn Tyr
            370                 375                 380

Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
                405                 410                 415

Lys Asn Phe Thr Gly Leu Phe Glu Phe Tyr Lys Leu Leu Cys Val Arg
                420                 425                 430

Gly Ile Ile Thr Ser Lys Thr Lys Ser Leu Asp Glu Gly Tyr Asn Lys
                435                 440                 445

Ala Leu Asn Asp Leu Cys Ile Lys Val Asn Asn Trp Asp Leu Phe Phe
450                 455                 460

Ser Pro Ser Glu Asp Asn Phe Thr Asn Asp Leu Asn Lys Gly Glu Glu
465                 470                 475                 480

Ile Thr Ser Asp Thr Asn Ile Glu Ala Ala Glu Asn Ile Ser Leu
                485                 490                 495

Asp Leu Ile Gln Gln Tyr Tyr Leu Thr Phe Asn Phe Asp Asn Glu Pro
                500                 505                 510

Glu Asn Ile Ser Ile Glu Asn Leu Ser Ser Asp Ile Ile Gly Gln Leu
                515                 520                 525

Glu Leu Met Pro Asn Ile Glu Arg Phe Pro Asn Gly Lys Lys Tyr Glu
                530                 535                 540

Leu Asp Lys Tyr Thr Met Phe His Tyr Leu Arg Ala Gln Glu Phe Glu
545                 550                 555                 560

His Gly Lys Ser Arg Ile Val Leu Thr Asn Ser Val Asn Glu Ala Leu
                565                 570                 575
```

-continued

Leu Asn Pro Ser Ser Val Tyr Thr Phe Phe Ser Ser Asp Tyr Val Arg
            580                 585                 590

Lys Val Asn Lys Ala Thr Glu Ala Met Phe Leu Gly Trp Val Glu
        595                 600                 605

Gln Leu Val Tyr Asp Phe Thr Asp Glu Thr Ser Glu Val Ser Thr Thr
            610                 615                 620

Asp Lys Ile Ala Asp Ile Thr Ile Ile Pro Tyr Ile Gly Pro Ala
625                 630                 635                 640

Leu Asn Ile Gly Asn Met Leu Tyr Lys Asp Asp Phe Val Gly Ala Leu
                645                 650                 655

Ile Phe Ser Gly Ala Val Ile Leu Leu Glu Phe Ile Pro Glu Ile Ala
                660                 665                 670

Ile Pro Val Leu Gly Thr Phe Ala Leu Val Ser Tyr Ile Ala Asn Lys
        675                 680                 685

Val Leu Thr Val Gln Thr Ile Asp Asn Ala Leu Ser Lys Arg Asn Glu
        690                 695                 700

Lys Trp Gly Glu Val Tyr Lys Tyr Ile Val Thr Asn Trp Leu Ala Lys
705                 710                 715                 720

Val Asn Thr Gln Ile Asp Leu Ile Arg Lys Lys Met Lys Glu Ala Leu
                725                 730                 735

Glu Asn Gln Ala Glu Ala Thr Lys Ala Ile Ile Asn Tyr Gln Tyr Asn
            740                 745                 750

Gln Tyr Thr Glu Glu Glu Lys Asn Asn Ile Asn Phe Asn Ile Gly Asp
        755                 760                 765

Leu Ser Ser Lys Leu Asn Asp Ser Ile Asn Lys Ala Met Ile Asn Ile
770                 775                 780

Asn Lys Phe Leu Asn Gln Cys Ser Val Ser Tyr Leu Met Asn Ser Met
785                 790                 795                 800

Ile Pro Tyr Gly Val Lys Arg Leu Glu Asp Phe Asp Ala Ser Leu Lys
                805                 810                 815

Asp Ala Leu Leu Lys Tyr Ile Tyr Asp Asn Arg Gly Thr Leu Ile Gly
            820                 825                 830

Gln Val Asp Arg Leu Lys Asp Lys Val Asn Asn Thr Leu Ser Thr Asp
        835                 840                 845

Ile Pro Phe Gln Leu Ser Lys Tyr Val Asp Asn Gln Arg Leu Leu Ser
850                 855                 860

Thr Phe Thr Glu Tyr Ile Lys Asn Ile Ile Asn Thr Ser Ile Leu Asn
865                 870                 875                 880

Leu Arg Tyr Glu Ser Asn His Leu Ile Asp Leu Ser Arg Tyr Ala Ser
                885                 890                 895

Glu Ile Asn Ile Gly Ser Lys Val Asn Phe Asp Pro Ile Asp Lys Asn
            900                 905                 910

Gln Ile Gln Leu Phe Asn Leu Glu Ser Ser Lys Ile Glu Ile Ile Leu
        915                 920                 925

Lys Asn Ala Ile Val Tyr Asn Ser Met Tyr Glu Asn Phe Ser Thr Ser
930                 935                 940

Phe Trp Ile Lys Ile Pro Lys Tyr Phe Ser Lys Ile Asn Leu Asn Asn
945                 950                 955                 960

Glu Tyr Thr Ile Ile Asn Cys Ile Glu Asn Asn Ser Gly Trp Lys Val
                965                 970                 975

Ser Leu Asn Tyr Gly Glu Ile Ile Trp Thr Leu Gln Asp Asn Lys Gln
            980                 985                 990

Asn Ile Gln Arg Val Val Phe Lys Tyr Ser Gln Met Val Ala Ile Ser
        995                 1000                1005

Asp Tyr Ile Asn Arg Trp Ile Phe Ile Thr Ile Thr Asn Asn Arg
    1010                1015                1020

Leu Asn Asn Ser Lys Ile Tyr Ile Asn Gly Arg Leu Ile Asp Gln
    1025                1030                1035

Lys Pro Ile Ser Asn Leu Gly Asn Ile His Ala Ser Asn Asn Ile
    1040                1045                1050

Met Phe Lys Leu Asp Gly Cys Arg Asp Pro Gln Arg Tyr Ile Trp
    1055                1060                1065

Ile Lys Tyr Phe Asn Leu Phe Asp Lys Glu Leu Asn Glu Lys Glu
    1070                1075                1080

Ile Lys Asp Leu Tyr Asp Asn Gln Ser Asn Ser Gly Ile Leu Lys
    1085                1090                1095

Asp Phe Trp Gly Asn Tyr Leu Gln Tyr Asp Lys Pro Tyr Tyr Met
    1100                1105                1110

Leu Asn Leu Tyr Asp Pro Asn Lys Tyr Val Asp Val Asn Asn Val
    1115                1120                1125

Gly Ile Arg Gly Tyr Met Tyr Leu Lys Gly Pro Arg Gly Ser Ile
    1130                1135                1140

Val Thr Thr Asn Ile Tyr Leu Asn Ser Ser Leu Tyr Met Gly Thr
    1145                1150                1155

Lys Phe Ile Ile Lys Lys Tyr Ala Ser Gly Asn Lys Asp Asn Ile
    1160                1165                1170

Val Arg Asn Asn Asp Arg Val Tyr Ile Asn Val Val Val Lys Asn
    1175                1180                1185

Lys Glu Tyr Arg Leu Ala Thr Asn Ala Ser Gln Ala Gly Val Glu
    1190                1195                1200

Lys Ile Leu Ser Val Leu Glu Ile Pro Asp Val Gly Asn Leu Ser
    1205                1210                1215

Gln Val Val Val Met Lys Ser Lys Asn Asp Gln Gly Ile Arg Asn
    1220                1225                1230

Lys Cys Lys Met Asn Leu Gln Asp Asn Asn Gly Asn Asp Ile Gly
    1235                1240                1245

Phe Ile Gly Phe His Gln Phe Asn Asn Ile Asp Lys Leu Val Ala
    1250                1255                1260

Ser Asn Trp Tyr Asn Arg Gln Ile Glu Arg Ser Ser Arg Thr Phe
    1265                1270                1275

Gly Cys Ser Trp Glu Phe Ile Pro Val Asp Asp Gly Trp Gly Glu
    1280                1285                1290

Ser Pro Leu
    1295

<210> SEQ ID NO 3
<211> LENGTH: 11703
<212> TYPE: DNA
<213> ORGANISM: Clostridium botulinum

<400> SEQUENCE: 3
attagtaata tctatatgca atcttatatt atagttattt aattctgtaa cttctacttt      60
taatatataa attgcaccat ttaataaacg tattgacttg gtactattta agagatttaa     120
attttgttgt atattaatta aattatagcc gtcaatagtt tcagtgactc taaataaagt     180
acctattcct tggttattac tagtataaag cctaatgtta gatgtatctt tattattaaa     240
gttaccaggt actgtaaatt catatgaaat atagttacca acatcaggac tttgtcttgt     300
atagtaatgt gcacctgttg aattaagatc atctattata ttaactgaag aattcattaa     360

-continued

| | | |
|---|---|---|
| atttcggaga tccccttctt ctctctcgaa ttttatttga ttttctatat tagaagaagt | 420 |
| ttgtggtact ctaatgtagt aattttatc cttattaagc aaaacaacta ataactttt | 480 |
| aacattagga ctgtcaaacc cagtaatata atttattgct ttaatatcat catcacataa | 540 |
| attcccagat tggaaatttc tattaccaga acctatcgct tcatatattt ttaatgatgg | 600 |
| tagattattc tgagcattaa ttttataaat tcctgtagta tttactgtaa ataatatata | 660 |
| aaatggatta ttatttacaa tacccggaat gttatatgtg taattatctg aaatagcagt | 720 |
| atttattttt tgtatatttt cagatgggtc tatgacacct actacgattt cttcctcggg | 780 |
| gccattctgt ataaacccat cttcagccac ttgcgtttta actacttcag attcaggtga | 840 |
| aggagcatta gttacttcac aatatcctaa ggaaggaagg taatactcag ctttattaac | 900 |
| aatacttcca ttttgatagt ctattaattc atacttttca taggtattat aagcctttat | 960 |
| gcatatattt ttatttgaag gagcttcttc tacaaattta ataacgatg ttgatgtatt | 1020 |
| aaataattgt acattgaaag cgtctttaag tctttcttca gtatattgtt gtgagaattt | 1080 |
| tgcatcatta cttgtggtga ataatggcct agttgtattt cttagtcgag gttgtataat | 1140 |
| acttcctgat gaacctgctt cgattaataa tgtacctatc aaatctttat catttgttct | 1200 |
| tatatatcca tcacccttat taataacata taatccatta ctataaggta atactcgttg | 1260 |
| tgtgctacta actttagaat taaaaatatt gttagttggt atattttag tagttctaa | 1320 |
| aatttttta tataggaatt gttcatttaa aatgcactta tcattagtta aaaagtaaaa | 1380 |
| atctttattt attttttccc ctggattaaa ttctatagac ttaacatatc caagagatgg | 1440 |
| aacatataaa actgctcttt ctataatttc atgttgcaag acttttatta tttcatatct | 1500 |
| aatgtaggta tattgtaaat acatatataa gttttattt gagggagcgg ttttactaaa | 1560 |
| ttcaaatcct attggaattt gattagcttc agtaaagtta gcaaatacag tttgtatatt | 1620 |
| attttttata tattcttcat tgaaggatgg tgttggataa taatatggta tcgcattatc | 1680 |
| atttacacgt aggtccccaa ctattcctgt tgatccatta ctaattacac ttccacctag | 1740 |
| tatttgattt tgtctagata atatccatcc atccctctg ctaactacat aattaccatc | 1800 |
| agctaaatca atagtatcac tatagtttat aacttttct tgtatatcat tataaatttt | 1860 |
| ttttatagat gaattcatac acttttctcc tttatatttt ttcaagtttg aacatttcat | 1920 |
| ttgaattgta tatcaaaaa ttaggtagta ggagtagtgg ttggcttaaa atatttat | 1980 |
| tagtatcata aatgtcccag gcataatcta attcattcac tttatttaaa cttaacataa | 2040 |
| tataagtatt tacagcgatt ttaatgggaa accagtagca tctattggat aatgaatcta | 2100 |
| aagaaataaa tccaaagtta tcgtaactta aatacttatt tggttctgct acattagaga | 2160 |
| ttttaaagca tctattttca gccatatatt ctacattcca ttttgatta tttgcagaag | 2220 |
| attcatttga aaatgttaat gatcctgata caggatttaa atataaagaa tcagaaaaga | 2280 |
| tagattttat attgtaatta ccattaggta gaaaagttct ttcaactgac atataattca | 2340 |
| cctctttata aattagatga tagtactcat attaaatttt tgttgatatt aattttatgg | 2400 |
| gttacgaata taccatttct gattattatc tccatgataa ttaaatactt gaatatcagt | 2460 |
| tccgtttgct gtttggctgt tatataaatc tagagcttta gttttatcgc gtagattagt | 2520 |
| aattgtatat gtttcataag tatctggaac aggatttata agccaatatt gggcatcatt | 2580 |
| attttgatca ttagaataaa cccttacagt attaccattt gaaaaaatcc atgttagaac | 2640 |
| tccgtttgaa agtatttcat taaaaaactg gtatgctgct ttttcttcat tatatctaat | 2700 |
| tgtccatttt tgattgcgat cattgttcca agtatataaa ttaacattta gatctgtcat | 2760 |

```
agctacttgt tgtacaactt tattagaagc taatattgga cttattttac atgtgaaatt    2820
gttaagatct gatattatat aatcttctat gataaatttt atataatttg aattattaag    2880
tgtgctaagt ttcaaattac gagctacggt atcggcatat aatactaagt tagggttttt    2940
ataacttgca ataataaatg aattgttacc aatgtctttt aataataacc aatattgatt    3000
atctgcattt gaatcttgtt gcgctgatat attatgtgtt ggtgcattcc atgttaaaac    3060
taaattagta ttatggatat tcatactttt tattttataa gcagctttat tagaatcata    3120
tataattctc catcttttcaa ggtaatttct agtttgttga ataagctaa cgttaccgtt    3180 accgtcaact tgataaaaaa ataaatctgt attagcctta caggagatgg taacgatttt    3240
gtcatttaat gaattttgga ttactgaatg gtgttccatt atgattcctc ctttatttaa    3300
taattaatct tacatataat ataaacata atgaaattat tttttgtaaa cctaaaattt    3360
aaaagcaatt agtttcttta tagtaaataa agtaataata tatatattat gggggggatag   3420 cggtaaatat gaataaattg tttttacaaa ttaaaatgtt gaaaatgac aacagagagt    3480 ttcaagaaat ttttaagcat tttgaaaaa ctatagatat atttactaga aaatataata    3540
tatatgataa ttacaatgat attttgtacc atttatggta tatacttaaa aaagttgatt   3600
tgagcaattt caatacacaa aatgatttag agagatatat tagtaggact ttaaaaagat    3660
attgcttaga tatttgcaat aaaagaaaga ttgataagaa aataatatat aattcagaaa    3720
ttgcagataa gaaattaagc ttaatagcaa atagttattc aagttattca gatttgaat    3780 ttaatgattt aatatccata ttacctgata atcaaaagaa aattatatat atgaaatttg    3840
ttgaagatat taaggagata gatatagcta aaaaacttaa tataagtcgt caatctgtat    3900
ataaaaataa aatactggct ttagagagat tagaacccat attgaaaaaa ttaattaata    3960
tgtagtttat atttttttaaa aattttaggt ttacaaaaaa tagtgtggct atgttatata    4020
taaatgataa caatatactg aaaaatatat ccaaaatta aggggcgtg tatagtaaat    4080 aattaaaagt atgtgcgttg aaataaattt aggagagtgg ttagatatga atataaatga    4140
caacttaagt ataaattccc cagtagataa taaaaatgtt gtagtagtta gagctagaaa    4200
aactgatacg ttttttaagg cttttaaggt tgctcctaat atttgggtgg cgccagagag    4260
atattatggc gaatctctga gtatagatga agaatataaa gttgatgggg gaatatatga    4320
ttctaatttt ctttcacaag atagtgaaaa agataagttc ttacaagcca ttattacttt    4380
gttaaaaaga attaataata ctaacgctgg ggaaaaatta ttatctttga tttctacagc    4440
tattccattt ccttatggat atataggtgg aggatattat gcacctaata tgattacttt    4500
tggatcagca ccaaaatcta ataaaaaatt gaattcttta atttcaagta ctattccatt    4560
tccttatgca ggatatagag aaacaaatta tctttcatct gaagataata aaagtttcta    4620
tgcatctaat atagttattt ttggtccagg agcaaacata gtagaaaaca atactgttt   4680 ttataaaaag gaagatgcag aaaatggtat gggaacaatg actgaaatat ggttccaacc    4740
atttctaacc tataaatatg accaattta tattgatcct gcaatagaat taatgaaatg    4800
tttaataaaa tctctttatt tcttatatgg gataaaacca agtgatgatt tagttgttcc    4860
atatagatta agaaatgaat tagagaatat agaatactca cagttggata tagttgattt    4920
actagtatcc ggaggcattg atcctaaatt tataaataca gatccatatt ggtttataga    4980
taattatttc tcaaatgcaa aaaaaatgtt tgaagatcat aggaatatttt atgaaacaga    5040 aattgaagga aataatgcca ttggtaatga tataaaattg agattaaaac aaaagtttcg    5100
aatcaatatc aatgatatat gggaattaaa tttaaattat ttctctaaag agtttaacat    5160
```

```
tatgatgcca gatagattta ataatgcact taaacatttt tatagaaaac aatactacaa   5220
aatagattac ccagaaaatt atagtataaa tggttttgtt aatggtcaaa ttaatgctca   5280
attatcttta tcagatagaa atcaagatat tataaataaa cctgaagaaa taattaattt   5340
attaaatgaa ataatgttt tattaatgag aagtaatatt tatggtgatg gattaaaaag   5400
cactgtagat gatttttaca gtaattataa atcccatat aatagagcct atgaatatca   5460
ttttaataat tcaaatgatt cttctttaga taatgttaac attggagtaa tagacaatat   5520
tccagagatt atagatgtaa atccttataa ggaaaattgt gataagtttt cgccggtaca   5580
gaaaattaca agtactagag aaattaatac aaatatacca tggcctataa attatttaca   5640
agctcaaaat accaacaatg aaaaatttag tttatcctca gattttgtag aagtagtttc   5700
ttctaaagat aaatctttag tgtattcttt cttatctaat gtaatgtttt atttagattc   5760
cataaaggat aatagtccta ttgatacaga taaaaaatat tatttatggt taagagagat   5820
ttttagaaat tattcttttg atattactgc aactcaagaa attaatacta attgcggtat   5880
taataaagta gtaacttggt ttggaaaagc attaaatatt ttaaatacat cagattcttt   5940
tgtagaagaa tttcaaaatt tagggccaag ttcacttatt aataaaaaag aaaatttaag   6000
tatgccaata attgagattt atgaaatccc taacgatatg ttaggattac cactaaatga   6060
tttaaatgaa aaattattta acatatattc taaaaataca gcttatttta aaaaaatcta   6120
ctataatttc ctagatcagt ggtggacaca atattatagt caatattttg atttaatttg   6180
tatggctaaa agatcagtgt tagctcaaga aactttaata aaaagaataa tacaaaaaaa   6240
attgagttat ttaataggaa attctaatat atcatctgat aacttagcat tgatgaatct   6300
tacaacaaca aatacattaa gagatatttc aaacgaatca caaatagcaa tgaataatgt   6360
agatagtttt ttaaataatg ccgctatatg tgtttttgaa agtaatatat atcctaaatt   6420
tatttctttt atggaacaat gtattaataa tataaaatatt aagacaaaag aatttataca   6480
aaaatgtact aatattaatg aagatgaaaa attacaatta attaaccaaa atgttttaa   6540 tagcttagat tttgaattct taaacattca aaatatgaaa agtttattta gttcagagac   6600
agcattactt ataaaggaag aaacttggcc ttatgaacta gtgttatatg cttttcagga   6660
atcaggtaat aatgttatcg gagatgcatc tggtaaaaat acatcaatag aatattctaa   6720
ggacataggt ttagtttatg gaataaatag tgatgcatta tatttaaatg gatctaatca   6780
aagtataagt ttttctaatg atttctttga aaatggatta actaatagtt tttcaattta   6840
tttttggttg agaaatttgg gcaaagatac tattaaatct aagttaatag gtagtaagga   6900 agataatttgt ggttgggaaa tttattttca agatactggg ttggttttta atatgataga   6960
ttctaatgga aatgagaaga atatatatct atctgatgtt tctaataata gttggcacta   7020
tataactata tctgtagatc gtttaaaaga acaattatta atatttattg atgataattt   7080
agtggctaat gaaagtatta agaaattttt aaatatctat tcaagtaata taatttcttt   7140
attaagcgag aataatccaa gttatattga gggattaact atttaaaata aacccactac   7200
aagtcagaaa gttttgagta attattttaa ggctctaaat aattcatata taagagacag   7260
tagtgaagaa cgattagaat acaataagac atatcaatta taattatg tattttcaga   7320 taagcctata tgtgaagtta acaaaataa taatatatat ttaacaatta ataatacaaa   7380
caatttaaat ttacaagctt ctaaatttaa attattaagt atcaatccaa ataaacaata   7440
tgttcaaaaa tttgatgagg taataatatc tatattagat aatatggaaa aatatataga   7500
tatatctgaa gataatagat tgcagctaat agacaacaaa aatagcgcaa agaagatgat   7560
```

```
aattagtaat gatatattta tttctaattg tttaactcta tcttgtggcg gtaaatatat    7620
atgtttatct atgaaagatg aaaccataa ttggatgata tgtaataatg atatgtcaaa    7680
gtatttgtat ttatggtcat ttaaataatt aataatttaa ttaattttaa atattataag    7740
aggtgttaaa tatgccattt gttaataaac aatttaatta taaagatcct gtaaatggtg    7800
ttgatattgc ttatataaaa attccaaatg caggacaaat gcaaccagta aaagctttta    7860
aaattcataa taaaatatgg gttattccag aaagagatac ctttacaaac cctgaagaag    7920
gagatttaaa tccaccacca gaagcaaaac aagttccagt ttcatattat gattcaacat    7980
atttaagtac agataatgaa aaagataatt atttaaaggg agttacaaaa ttatttgaga    8040
gaatttattc aactgagctt ggaagaatgt tgttaacatc aatagtaagg ggaataccat    8100
tttggggtgg aagtacaata gatacagaat taaaagttat tgatactaat tgtattaatg    8160
tgatacaacc agatggtagt tatagatcag aagaacttaa tctagtaata ataggaccct    8220
cagctgatat tatacagttt gaatgtaaaa gctttggaca tgacgttttg aatcttacgc    8280
gaaatggtta tggctctact caatacatta gatttagccc agattttaca tttggttttg    8340
aggagtcact tgaagttgat acaaatcctc ttttaggtgc aggcaaattt gctacagatc    8400
cagcagtaac attagcacat gaacttatac atgctggaca tagattatat ggaatagcaa    8460
ttaatccaaa tagggtttt aaagtaaata ctaatgccta ttatgaaatg agtgggttag    8520
aagtaagctt tgaggaactt agaacatttg gggaacatga tgcaaagttt atagatagtt    8580
tacaggaaaa cgaatttcgt ctatattatt ataataagtt taaagatata gcaagtacac    8640
ttaataaagc taaatcaata gtaggtacta ctgcttcatt acagtatatg aaaaatgttt    8700
ttaaagagaa atatctccta tctgaagata catctggaaa atttttcggta gataaattaa    8760 aatttgataa gttatacaaa atgttaacag agatttacac agaggataat tttgttaagt    8820
tttttaaagt acttaacaga aaaacatatt tgaattttga taaagccgta tttaagataa    8880
atatagtacc tgaggtaaat tacacaatat atgatggatt taatttaaga aatacaaatt    8940
tagcagcaaa cttaatggt caaaatacag aaattaataa tatgaatttt actaaactaa    9000 aaaatttac tggattgttt gaatttata agttgctatg tgtaagaggg ataataactt    9060
ctaaaactaa atcattagat gaaggataca ataaggcatt aaatgattta tgtatcaaag    9120
ttaataattg ggacttgttc tttagtcctt cagaagataa ttttactaat gatctaaata    9180
aaggagaaga aattacatct gatactaata tagaagcagc agaagaaaat attagtttag    9240
atttaataca acaatattat ttaacccttta attttgataa tgaacctgaa atatttcaa    9300 tagaaaatct ttcaagtgac attataggcc aattagaact tatgcctaat atagaaagat    9360
ttcctaatgg aaaaaagtat gagttagata aatatactat gttccattat cttcgtgctc    9420
aagaatttga acatggtaaa tctaggattg ttttaacaaa ttctgttaac gaagcattat    9480
taaatcctag tagtgtttat acatttttt cttcagacta tgtaaggaaa gttaataaag    9540
ctacggaggc agctatgttt ttaggctggg tagaacaatt agtatatgat tttaccgatg    9600
aaactagcga agtaagtact acggataaaa ttgcagatat aactataatt attccatata    9660
taggacctgc tttaaatata ggtaatatgt tatataaaga tgattttgta ggtgctttaa    9720
tattttcagg agctgttatt ctgttagaat ttataccaga gattgcaata cctgtattag    9780
gtacttttgc acttgtatca tatattgcga ataaggttct aactgttcaa acaatagata    9840
atgctttaag taaagaaaat gaaaatgggg gcgaggtcta taaatatata gtaacaaatt    9900
ggttagcaaa ggttaataca cagattgatc taataagaaa aaaaatgaaa gaagctttag    9960
```

| | |
|---|---|
| aaaatcaagc agaagcaaca aaggctataa taaactatca gtataatcaa tatactgagg | 10020 |
| aagagaaaaa taatattaat tttaatattg gtgatttaag ttcgaaactt aatgactcta | 10080 |
| taaataaagc tatgattaat ataaataaat ttttgaatca gtgctctgtt tcatatttaa | 10140 |
| tgaattctat gataccttat ggtgttaaac ggttagaaga ttttgatgct agtcttaaag | 10200 |
| atgcattatt aaagtatata tatgataata gaggaacttt aattggtcaa gtagatagat | 10260 |
| taaaagataa agttaataat acacttagta cagatatacc ttttcagctt tccaaatacg | 10320 |
| tagataatca agattatta tctacattta ctgaatatat taagaatatt attaatactt | 10380 |
| ctatattgaa tttaagatat gaaagtaatc atttaataga cttatctagg tatgcatcag | 10440 |
| aaataaaatat tggtagtaaa gtaaattttg atccaataga taaaaatcaa attcaattat | 10500 |
| ttaatttaga aagtagtaaa attgagataa ttttaaaaaa tgctattgta tataaatagta | 10560 |
| tgtatgaaaa ttttagtact agcttttgga taaaaattcc taagtatttt agcaagataa | 10620 |
| atctaaataa tgaatataca ataataaatt gtatagaaaa taattcagga tggaaagtat | 10680 |
| cacttaatta tggtgaaata atctggactt tgcaggataa taagcaaaac atacaaagag | 10740 |
| tagttttaa atacagtcaa atggttgcta tatcagatta tataaacaga tggatttta | 10800 |
| taactatcac taataataga ttaaataact ctaaaattta tataaatgga agattaatag | 10860 |
| atcaaaaacc aatttcaaat ttaggtaata ttcatgctag taataatata atgtttaaat | 10920 |
| tagatggttg tagagatcca caaagataca tttggataaa atattttaat cttttcgata | 10980 |
| aagaattaaa tgaaaagaa atcaaagatt tatatgataa tcaatcaaat tcaggtattt | 11040 |
| taaaagactt ttgggggtaat tatttacaat atgataaacc atactatatg ttaaatttat | 11100 |
| atgatccaaa taaatatgtc gatgtaaata atgtaggtat tagaggttat atgtatctta | 11160 |
| aagggcctag aggtagcata gtgactacaa acatttattt aaattcaagt ttgtatatgg | 11220 |
| ggacaaaatt tattataaaa aaatatgctt ctggaaataa agataatatt gttagaaata | 11280 |
| atgatcgtgt atatattaat gtagtagtta aaaataaaga atataggtta gctactaatg | 11340 |
| catcacaggc aggcgtagaa aaaatactaa gtgtattaga aatacctgat gtaggaaatc | 11400 |
| taagtcaagt agtagtaatg aagtcaaaaa atgatcaagg aataagaaat aaatgcaaaa | 11460 |
| tgaatttaca agataataat gggaatgata taggctttat aggattccat cagtttaata | 11520 |
| atatagataa actagtagca agtaattggt ataatagaca aatagaaaga tctagtagga | 11580 |
| cttttggttg ctcatgggaa tttattcctg tagatgatgg atggggagaa agtccactgt | 11640 |
| aattaatctc aaactacatg agtctgtcaa gaattttgtg taaacatcca taaaaattt | 11700 |
| aaa | 11703 |

<210> SEQ ID NO 4
<211> LENGTH: 1878
<212> TYPE: DNA
<213> ORGANISM: Clostridium botulinum

<400> SEQUENCE: 4

| | |
|---|---|
| atgaattcat ctataaaaaa aatttataat gatatacaag aaaaagttat aaactatagt | 60 |
| gatactattg atttagctga tggtaattat gtagttagca gaggggatgg atggatatta | 120 |
| tctagacaaa atcaaatact aggtggaagt gtaattagta atggatcaac aggaatagtt | 180 |
| ggggacctac gtgtaaatga atatgcgata ccatattatt atccaacacc atccttcaat | 240 |
| gaagaatata taaaaaataa tatacaaact gtatttgcta actttactga agctaatcaa | 300 |
| attccaatag gatttgaatt tagtaaaaacc gctcccctcaa ataaaaactt atatatgtat | 360 |

-continued

```
ttacaatata cctacattag atatgaaata ataaaagtct tgcaacatga aattatagaa      420
agagcagttt tatatgttcc atctcttgga tatgttaagt ctatagaatt taatccaggg      480
gaaaaaataa ataagagatt ttacttttta actaatgata agtgcatttt aaatgaacaa      540
ttcctatata aaaaaatttt agaaactact aaaaatatac caactaacaa tatttttaat      600
tctaaagtta gtagcacaca acgagtatta ccttatagta atggattata tgttattaat      660
aagggtgatg gatatataag aacaaatgat aaagatttga taggtacatt attaatcgaa      720
gcaggttcat caggaagtat tatacaacct cgactaagaa atacaactag gccattattc      780
accacaagta atgatgcaaa attctcacaa caatatactg aagaaagact taaagacgct      840
ttcaatgtac aattatttaa tacatcaaca tcgttattta aatttgtaga agaagctcct      900
tcaaataaaa atatatgcat aaaggcttat aatacctatg aaaagtatga attaatagac      960
tatcaaaatg gaagtattgt taataaagct gagtattacc ttccttcctt aggatattgt     1020
gaagtaacta atgctccttc acctgaatct gaagtagtta aaacgcaagt ggctgaagat     1080
gggtttatac agaatggccc cgaggaagaa atcgtagtag gtgtcataga cccatctgaa     1140
aatatacaaa aaataaatac tgctatttca gataattaca catataacat tccgggtatt     1200
gtaaataata atccattttta tatattattt acagtaaata ctacaggaat ttataaaatt     1260
aatgctcaga taatctacc atcattaaaa atatatgaag cgataggttc tggtaataga     1320
aatttccaat ctgggaattt atgtgatgat gatattaaag caataaatta tattactggg     1380
tttgacagtc ctaatgttaa aagttattta gttgttttgc ttaataagga taaaaattac     1440
tacattagag taccacaaac ttcttctaat atagaaaatc aaataaaatt cgagagagaa     1500 gaagggggatc tccgaaattt aatgaattct cagttaata taatagatga tcttaattca     1560
acaggtgcac attactatac aagacaaagt cctgatgttg gtaactatat tcatatgaa      1620 tttacagtac ctggtaactt taataataaa gatacatcta acattaggct ttatactagt     1680
aataaccaag gaataggtac tttatttaga gtcactgaaa ctattgacgg ctataattta     1740
attaatatac aacaaatttt aaatctctta aatagtacca agtcaatacg tttattaaat     1800
ggtgcaattt atatattaaa agtagaagtt acagaattaa ataactataa tataagattg     1860
catatagata ttactaat                                                   1878
```

<210> SEQ ID NO 5
<211> LENGTH: 626
<212> TYPE: PRT
<213> ORGANISM: Clostridium botulinum

<400> SEQUENCE: 5

```
Met Asn Ser Ser Ile Lys Lys Ile Tyr Asn Asp Ile Gln Glu Lys Val
1               5                   10                  15

Ile Asn Tyr Ser Asp Thr Ile Asp Leu Ala Asp Gly Asn Tyr Val Val
            20                  25                  30

Ser Arg Gly Asp Gly Trp Ile Leu Ser Arg Gln Asn Gln Ile Leu Gly
        35                  40                  45

Gly Ser Val Ile Ser Asn Gly Ser Thr Gly Ile Val Gly Asp Leu Arg
    50                  55                  60

Val Asn Asp Asn Ala Ile Pro Tyr Tyr Pro Thr Pro Ser Phe Asn
65                  70                  75                  80

Glu Glu Tyr Ile Lys Asn Asn Ile Gln Thr Val Phe Ala Asn Phe Thr
                85                  90                  95

Glu Ala Asn Gln Ile Pro Ile Gly Phe Glu Phe Ser Lys Thr Ala Pro
```

```
                   100                 105                 110
Ser Asn Lys Asn Leu Tyr Met Tyr Leu Gln Tyr Thr Tyr Ile Arg Tyr
            115                 120                 125
Glu Ile Ile Lys Val Leu Gln His Glu Ile Glu Arg Ala Val Leu
            130                 135                 140
Tyr Val Pro Ser Leu Gly Tyr Val Lys Ser Ile Glu Phe Asn Pro Gly
145                 150                 155                 160
Glu Lys Ile Asn Lys Asp Phe Tyr Phe Leu Thr Asn Asp Lys Cys Ile
            165                 170                 175
Leu Asn Glu Gln Phe Leu Tyr Lys Lys Ile Leu Glu Thr Thr Lys Asn
            180                 185                 190
Ile Pro Thr Asn Asn Ile Phe Asn Ser Lys Val Ser Ser Thr Gln Arg
            195                 200                 205
Val Leu Pro Tyr Ser Asn Gly Leu Tyr Val Ile Asn Lys Gly Asp Gly
            210                 215                 220
Tyr Ile Arg Thr Asn Asp Lys Asp Leu Ile Gly Thr Leu Leu Ile Glu
225                 230                 235                 240
Ala Gly Ser Ser Gly Ser Ile Ile Gln Pro Arg Leu Arg Asn Thr Thr
            245                 250                 255
Arg Pro Leu Phe Thr Thr Ser Asn Asp Ala Lys Phe Ser Gln Gln Tyr
            260                 265                 270
Thr Glu Glu Arg Leu Lys Asp Ala Phe Asn Val Gln Leu Phe Asn Thr
            275                 280                 285
Ser Thr Ser Leu Phe Lys Phe Val Glu Glu Ala Pro Ser Asn Lys Asn
            290                 295                 300
Ile Cys Ile Lys Ala Tyr Asn Thr Tyr Glu Lys Tyr Glu Leu Ile Asp
305                 310                 315                 320
Tyr Gln Asn Gly Ser Ile Val Asn Lys Ala Glu Tyr Tyr Leu Pro Ser
            325                 330                 335
Leu Gly Tyr Cys Glu Val Thr Asn Ala Pro Ser Pro Gly Ser Glu Val
            340                 345                 350
Val Lys Thr Gln Val Ala Glu Asp Gly Phe Ile Gln Asn Gly Pro Glu
            355                 360                 365
Glu Glu Ile Val Val Gly Val Ile Asp Pro Ser Glu Asn Ile Gln Lys
            370                 375                 380
Ile Asn Thr Ala Ile Ser Asp Asn Tyr Thr Tyr Asn Ile Pro Gly Ile
385                 390                 395                 400
Val Asn Asn Asn Pro Phe Tyr Ile Leu Phe Thr Val Asn Thr Thr Gly
            405                 410                 415
Ile Tyr Lys Ile Asn Ala Gln Asn Asn Leu Pro Ser Leu Lys Ile Tyr
            420                 425                 430
Glu Ala Ile Gly Ser Gly Asn Arg Asn Phe Gln Ser Gly Asn Leu Cys
            435                 440                 445
Asp Asp Asp Ile Lys Ala Ile Asn Tyr Ile Thr Gly Phe Asp Ser Pro
            450                 455                 460
Asn Val Lys Ser Tyr Leu Val Val Leu Leu Asn Lys Asp Lys Asn Tyr
465                 470                 475                 480
Tyr Ile Arg Val Pro Gln Thr Ser Ser Asn Ile Glu Asn Gln Ile Lys
            485                 490                 495
Phe Glu Arg Glu Glu Gly Asp Leu Arg Asn Leu Met Asn Ser Ser Val
            500                 505                 510
Asn Ile Ile Asp Asp Leu Asn Ser Thr Gly Ala His Tyr Tyr Thr Arg
            515                 520                 525
```

-continued

```
Gln Ser Pro Asp Val Gly Asn Tyr Ile Ser Tyr Glu Phe Thr Val Pro
    530                 535                 540

Gly Asn Phe Asn Asn Lys Asp Thr Ser Asn Ile Arg Leu Tyr Thr Ser
545                 550                 555                 560

Asn Asn Gln Gly Ile Gly Thr Leu Phe Arg Val Thr Glu Thr Ile Asp
                565                 570                 575

Gly Tyr Asn Leu Ile Asn Ile Gln Gln Asn Leu Asn Leu Leu Asn Ser
            580                 585                 590

Thr Lys Ser Ile Arg Leu Leu Asn Gly Ala Ile Tyr Ile Leu Lys Val
        595                 600                 605

Glu Val Thr Glu Leu Asn Asn Tyr Asn Ile Arg Leu His Ile Asp Ile
    610                 615                 620

Thr Asn
625

<210> SEQ ID NO 6
<211> LENGTH: 438
<212> TYPE: DNA
<213> ORGANISM: Clostridium botulinum

<400> SEQUENCE: 6
atgtcagttg aaagaacttt tctacctaat ggtaattaca atataaaatc tatcttttct      60
gattctttat atttaaatcc tgtatcagga tcattaacat tttcaaatga atcttctgca     120
aataatcaaa atggaatgt agaatatatg gctgaaaata gatgctttaa aatctctaat     180
gtagcagaac caaataagta tttaagttac gataactttg gatttatttc tttagattca     240
ttatccaata gatgctactg gtttcccatt aaaatcgctg taaatactta tattatgtta     300
agtttaaata agtgaatga attagattat gcctgggaca tttatgatac taataaaaat     360
attttaagcc aaccactact cctactacct aattttgata tatacaattc aaatgaaatg     420
ttcaaacttg aaaaaata                                                   438

<210> SEQ ID NO 7
<211> LENGTH: 146
<212> TYPE: PRT
<213> ORGANISM: Clostridium botulinum

<400> SEQUENCE: 7

Met Ser Val Glu Arg Thr Phe Leu Pro Asn Gly Asn Tyr Asn Ile Lys
1               5                   10                  15

Ser Ile Phe Ser Asp Ser Leu Tyr Leu Asn Pro Val Ser Gly Ser Leu
            20                  25                  30

Thr Phe Ser Asn Glu Ser Ser Ala Asn Asn Gln Lys Trp Asn Val Glu
        35                  40                  45

Tyr Met Ala Glu Asn Arg Cys Phe Lys Ile Ser Asn Val Ala Glu Pro
    50                  55                  60

Asn Lys Tyr Leu Ser Tyr Asp Asn Phe Gly Phe Ile Ser Leu Asp Ser
65                  70                  75                  80

Leu Ser Asn Arg Cys Tyr Trp Phe Pro Ile Lys Ile Ala Val Asn Thr
                85                  90                  95

Tyr Ile Met Leu Ser Leu Asn Lys Val Asn Glu Leu Asp Tyr Ala Trp
            100                 105                 110

Asp Ile Tyr Asp Thr Asn Lys Asn Ile Leu Ser Gln Pro Leu Leu Leu
        115                 120                 125

Leu Pro Asn Phe Asp Ile Tyr Asn Ser Asn Glu Met Phe Lys Leu Glu
    130                 135                 140
```

Lys Ile
145

<210> SEQ ID NO 8
<211> LENGTH: 882
<212> TYPE: DNA
<213> ORGANISM: Clostridium botulinum

<400> SEQUENCE: 8

| | |
|---|---|
| atggaacacc attcagtaat ccaaaattca ttaaatgaca aaatcgttac catctcctgt | 60 |
| aaggctaata cagatttatt tttttatcaa gttgacggta acggtaacgt tagcttattt | 120 |
| caacaaacta gaaattacct tgaaagatgg agaattatat atgattctaa taaagctgct | 180 |
| tataaaataa aaagtatgaa tatccataat actaatttag ttttaacatg gaatgcacca | 240 |
| acacataata tatcagcgca acaagattca aatgcagata atcaatattg gttattatta | 300 |
| aaagacattg gtaacaattc atttattatt gcaagttata aaaaccctaa cttagtatta | 360 |
| tatgccgata ccgtagctcg taatttgaaa cttagcacac ttaataattc aaattatata | 420 |
| aaatttatca tagaagatta tataatatca gatcttaaca atttcacatg taaaataagt | 480 |
| ccaatattag cttctaataa agttgtacaa caagtagcta tgacagatct aaatgttaat | 540 |
| ttatatactt ggaacaatga tcgcaatcaa aaatggacaa ttagatataa tgaagaaaaa | 600 |
| gcagcatacc agtttttaa tgaaatactt tcaacggag ttctaacatg gatttttca | 660 |
| aatggtaata ctgtaagggt ttattctaat gatcaaaata tgatgccca atattggctt | 720 |
| ataaatcctg ttccagatac ttatgaaaca tatacaatta ctaatctacg cgataaaact | 780 |
| aaagctctag atttatataa cagccaaaca gcaaacggaa ctgatattca agtatttaat | 840 |
| tatcatggag ataataatca gaaatggtat attcgtaacc ca | 882 |

<210> SEQ ID NO 9
<211> LENGTH: 294
<212> TYPE: PRT
<213> ORGANISM: Clostridium botulinum

<400> SEQUENCE: 9

Met Glu His His Ser Val Ile Gln Asn Ser Leu Asn Asp Lys Ile Val
1               5                  10                  15

Thr Ile Ser Cys Lys Ala Asn Thr Asp Leu Phe Phe Tyr Gln Val Asp
            20                  25                  30

Gly Asn Gly Asn Val Ser Leu Phe Gln Gln Thr Arg Asn Tyr Leu Glu
        35                  40                  45

Arg Trp Arg Ile Ile Tyr Asp Ser Asn Lys Ala Ala Tyr Lys Ile Lys
    50                  55                  60

Ser Met Asn Ile His Asn Thr Asn Leu Val Leu Thr Trp Asn Ala Pro
65                  70                  75                  80

Thr His Asn Ile Ser Ala Gln Gln Asp Ser Asn Ala Asp Asn Gln Tyr
            85                  90                  95

Trp Leu Leu Leu Lys Asp Ile Gly Asn Asn Ser Phe Ile Ile Ala Ser
        100                 105                 110

Tyr Lys Asn Pro Asn Leu Val Leu Tyr Ala Asp Thr Val Ala Arg Asn
    115                 120                 125

Leu Lys Leu Ser Thr Leu Asn Asn Ser Asn Tyr Ile Lys Phe Ile Ile
        130                 135                 140

Glu Asp Tyr Ile Ile Ser Asp Leu Asn Asn Phe Thr Cys Lys Ile Ser
145                 150                 155                 160

Pro Ile Leu Ala Ser Asn Lys Val Val Gln Gln Val Ala Met Thr Asp

```
                165                 170                 175
Leu Asn Val Asn Leu Tyr Thr Trp Asn Asp Arg Asn Gln Lys Trp
            180                 185                 190

Thr Ile Arg Tyr Asn Glu Glu Lys Ala Ala Tyr Gln Phe Phe Asn Glu
            195                 200                 205

Ile Leu Ser Asn Gly Val Leu Thr Trp Ile Phe Ser Asn Gly Asn Thr
            210                 215                 220

Val Arg Val Tyr Ser Asn Asp Gln Asn Asp Ala Gln Tyr Trp Leu
225                 230                 235                 240

Ile Asn Pro Val Pro Asp Thr Tyr Glu Thr Tyr Thr Ile Thr Asn Leu
            245                 250                 255

Arg Asp Lys Thr Lys Ala Leu Asp Leu Tyr Asn Ser Gln Thr Ala Asn
            260                 265                 270

Gly Thr Asp Ile Gln Val Phe Asn Tyr His Gly Asp Asn Asn Gln Lys
            275                 280                 285

Trp Tyr Ile Arg Asn Pro
            290

<210> SEQ ID NO 10
<211> LENGTH: 534
<212> TYPE: DNA
<213> ORGANISM: Clostridium botulinum

<400> SEQUENCE: 10
atgaataaat tgttttttaca aattaaaatg ttgaaaaatg acaacagaga gtttcaagaa      60
atttttaagc attttgaaaa aactatagat atatttacta gaaaatataa tatatatgat     120
aattacaatg atattttgta ccatttatgg tatatactta aaaagttga tttgagcaat      180 ttcaatacac aaaatgattt agagagatat attagtagga ctttaaaaag atattgctta     240
gatatttgca ataaaagaaa gattgataag aaaataatat ataattcaga aattgcagat     300
aagaaattaa gcttaatagc aaatagttat tcaagttatt cagaatttga atttaatgat     360
ttaatatcca tattacctga taatcaaaag aaaattatat atgaaaatt tgttgaagat     420 attaaggaga tagatatagc taaaaaactt aatataagtc gtcaatctgt atataaaaat     480
aaaatactgg ctttagagag attagaaccc atattgaaaa aattaattaa tatg          534

<210> SEQ ID NO 11
<211> LENGTH: 178
<212> TYPE: PRT
<213> ORGANISM: Clostridium botulinum

<400> SEQUENCE: 11

Met Asn Lys Leu Phe Leu Gln Ile Lys Met Leu Lys Asn Asp Asn Arg
1               5                   10                  15

Glu Phe Gln Glu Ile Phe Lys His Phe Glu Lys Thr Ile Asp Ile Phe
                20                  25                  30

Thr Arg Lys Tyr Asn Ile Tyr Asp Asn Tyr Asn Asp Ile Leu Tyr His
            35                  40                  45

Leu Trp Tyr Ile Leu Lys Lys Val Asp Leu Ser Asn Phe Asn Thr Gln
        50                  55                  60

Asn Asp Leu Glu Arg Tyr Ile Ser Arg Thr Leu Lys Arg Tyr Cys Leu
65                  70                  75                  80

Asp Ile Cys Asn Lys Arg Lys Ile Asp Lys Lys Ile Ile Tyr Asn Ser
                85                  90                  95

Glu Ile Ala Asp Lys Lys Leu Ser Leu Ile Ala Asn Ser Tyr Ser Ser
            100                 105                 110
```

Tyr Ser Glu Phe Glu Phe Asn Asp Leu Ile Ser Ile Leu Pro Asp Asn
            115                 120                 125

Gln Lys Lys Ile Ile Tyr Met Lys Phe Val Glu Asp Ile Lys Glu Ile
        130                 135                 140

Asp Ile Ala Lys Lys Leu Asn Ile Ser Arg Gln Ser Val Tyr Lys Asn
145                 150                 155                 160

Lys Ile Leu Ala Leu Glu Arg Leu Glu Pro Ile Leu Lys Lys Leu Ile
            165                 170                 175

Asn Met

<210> SEQ ID NO 12
<211> LENGTH: 3579
<212> TYPE: DNA
<213> ORGANISM: Clostridium botulinum

<400> SEQUENCE: 12

| | | | | | |
|---|---|---|---|---|---|
| atgaatataa | atgacaactt | aagtataaat | tccccagtag | ataataaaaa | tgttgtagta | 60 |
| gttagagcta | gaaaaactga | tacgtttttt | aaggctttta | aggttgctcc | taatatttgg | 120 |
| gtggcgccag | agagatatta | tggcgaatct | ctgagtatag | atgaagaata | taagttgat | 180 |
| gggggaatat | atgattctaa | ttttcttca | caagatagtg | aaaagataa | gttcttacaa | 240 |
| gccattatta | ctttgttaaa | aagaattaat | aatactaacg | ctggggaaaa | attattatct | 300 |
| ttgatttcta | cagctattcc | atttccttat | ggatatatag | gtggaggata | ttatgcacct | 360 |
| aatatgatta | cttttggatc | agcaccaaaa | tctaataaaa | aattgaattc | tttaatttca | 420 |
| agtactattc | catttcctta | tgcaggatat | agagaaacaa | attatctttc | atctgaagat | 480 |
| aataaaagtt | tctatgcatc | taatatagtt | attttggtc | caggagcaaa | catagtagaa | 540 |
| aacaatactg | ttttttataa | aaggaagat | gcagaaaatg | gtatgggaac | aatgactgaa | 600 |
| atatggttcc | aaccatttct | aacctataaa | tatgaccaat | tttatattga | tcctgcaata | 660 |
| gaattaatga | atgtttaat | aaaatctctt | tatttcttat | atgggataaa | accaagtgat | 720 |
| gatttagttg | ttccatatag | attaagaaat | gaattagaga | atatagaata | ctcacagttg | 780 |
| gatatagttg | atttactagt | atccggaggc | attgatccta | aatttataaa | tacagatcca | 840 |
| tattggttta | tagataatta | ttctcaaat | gcaaaaaaa | tgtttgaaga | tcataggaat | 900 |
| atttatgaaa | cagaaattga | aggaaataat | gccattggta | atgatataaa | attgagatta | 960 |
| aaacaaaagt | ttcgaatcaa | tatcaatgat | atatgggaat | taaatttaaa | ttatttctct | 1020 |
| aaagagttta | acattatgat | gccagataga | tttaataatg | cacttaaaca | ttttatagaa | 1080 |
| aaacaatact | acaaaataga | ttacccagaa | aattatagta | aaatggtttt | tgttaatggt | 1140 |
| caaattaatg | ctcaattatc | tttatcagat | agaaatcaag | atattataaa | taaacctgaa | 1200 |
| gaaataatta | atttattaaa | tgaaaataat | gttttattaa | tgagaagtaa | tatttatggt | 1260 |
| gatggattaa | aaagcactgt | agatgatttt | tacagtaatt | ataaaatccc | ataataga | 1320 |
| gcctatgaat | atcatttaa | taattcaaat | gattcttctt | tagataatgt | taacattgga | 1380 |
| gtaatagaca | atattccaga | gattatagat | gtaaatcctt | ataaggaaaa | ttgtgataag | 1440 |
| ttttcgccgg | tacagaaaat | tacaagtact | agagaaatta | atacaaatat | accatggcct | 1500 |
| ataaattatt | tacaagctca | aaataccaac | aatgaaaaat | ttagtttatc | ctcagatttt | 1560 |
| gtagaagtag | tttcttctaa | agataaatct | ttagtgtatt | ctttcttatc | taatgtaatg | 1620 |
| ttttatttag | attccataaa | ggataatagt | cctattgata | cagataaaaa | atattattta | 1680 |
| tggttaagag | agatttttag | aaattattct | tttgatatta | ctgcaactca | agaaattaat | 1740 |

```
actaattgcg gtattaataa agtagtaact tggtttggaa aagcattaaa tattttaaat    1800
acatcagatt cttttgtaga agaatttcaa aatttagggc caagttcact tattaataaa    1860
aaagaaaatt taagtatgcc aataattgag atttatgaaa tccctaacga tatgttagga    1920
ttaccactaa atgatttaaa tgaaaaatta tttaacatat attctaaaaa tacagcttat    1980
tttaaaaaaa tctactataa tttcctagat cagtggtgga cacaatatta tagtcaatat    2040
tttgatttaa tttgtatggc taaaagatca gtgttagctc aagaaacttt aataaaaaga    2100
ataatacaaa aaaaattgag ttatttaata ggaaattcta atatatcatc tgataactta    2160
gcattgatga atcttacaac aacaaataca ttaagagata tttcaaacga atcacaaata    2220
gcaatgaata atgtagatag tttttttaaat aatgccgcta tatgtgtttt tgaaagtaat    2280
atatatccta aatttatttc ttttatggaa caatgtatta ataatataaa tattaagaca    2340
aaagaattta tacaaaaatg tactaatatt aatgaagatg aaaaattaca attaattaac    2400
caaaatgttt ttaatagctt agatttttgaa ttcttaaaca ttcaaaatat gaaaagttta    2460
tttagttcag agacagcatt acttataaag gaagaaactt ggccttatga actagtgtta    2520
tatgcttttc aggaatcagg taataatgtt atcggagatg catctggtaa aaatacatca    2580
atagaatatt ctaaggacat aggtttagtt tatggaataa atagtgatgc attatattta    2640
aatggatcta atcaaagtat aagttttcct aatgatttct ttgaaaatgg attaactaat    2700
agttttcaa tttatttttg gttgagaaat ttgggcaaag atactattaa atctaagtta    2760
ataggtagta aggaagataa ttgtggttgg gaaatttatt ttcaagatac tgggttggtt    2820
tttaatatga tagattctaa tggaaatgag aagaatatat atctatctga tgtttctaat    2880
aatagttggc actatataac tatatctgta gatcgtttaa aagaacaatt attaatattt    2940
attgatgata atttagtggc taatgaaagt attaaagaaa ttttaaatat ctattcaagt    3000
aatataattt cttttattaag cgagaataat ccaagttata ttgagggatt aactatttta    3060
aataaaccca ctacaagtca gaaagttttg agtaattatt ttaaggctct aaataattca    3120
tatataagag acagtagtga agaacgatta gaatacaata agacatatca attatataat    3180
tatgtatttt cagataagcc tatatgtgaa gttaaacaaa ataataatat atatttaaca    3240
attaataata caaacaattt aaatttacaa gcttctaaat ttaaattatt aagtatcaat    3300
ccaaataaac aatatgttca aaaatttgat gaggtaataa tatctatatt agataatatg    3360
gaaaaatata tagatatatc tgaagataat agattgcagc taatagacaa caaaaatagc    3420
gcaaagaaga tgataattag taatgatata tttatttcta attgtttaac tctatcttgt    3480
ggcggtaaat atatatgttt atctatgaaa gatgaaaacc ataattggat gatatgtaat    3540
aatgatatgt caaagtattt gtatttatgg tcatttaaa                           3579
```

<210> SEQ ID NO 13
<211> LENGTH: 1193
<212> TYPE: PRT
<213> ORGANISM: Clostridium botulinum

<400> SEQUENCE: 13

Met Asn Ile Asn Asp Asn Leu Ser Ile Asn Ser Pro Val Asp Asn Lys
1               5                   10                  15

Asn Val Val Val Val Arg Ala Arg Lys Thr Asp Thr Phe Phe Lys Ala
                20                  25                  30

Phe Lys Val Ala Pro Asn Ile Trp Val Ala Pro Glu Arg Tyr Tyr Gly
            35                  40                  45

-continued

```
Glu Ser Leu Ser Ile Asp Glu Glu Tyr Lys Val Asp Gly Gly Ile Tyr
 50                  55                  60

Asp Ser Asn Phe Leu Ser Gln Asp Ser Glu Lys Asp Lys Phe Leu Gln
 65                  70                  75                  80

Ala Ile Ile Thr Leu Leu Lys Arg Ile Asn Asn Thr Asn Ala Gly Glu
                 85                  90                  95

Lys Leu Leu Ser Leu Ile Ser Thr Ala Ile Pro Phe Pro Tyr Gly Tyr
                100                 105                 110

Ile Gly Gly Gly Tyr Tyr Ala Pro Asn Met Ile Thr Phe Gly Ser Ala
            115                 120                 125

Pro Lys Ser Asn Lys Lys Leu Asn Ser Leu Ile Ser Ser Thr Ile Pro
130                 135                 140

Phe Pro Tyr Ala Gly Tyr Arg Glu Thr Asn Tyr Leu Ser Ser Glu Asp
145                 150                 155                 160

Asn Lys Ser Phe Tyr Ala Ser Asn Ile Val Ile Phe Gly Pro Gly Ala
                165                 170                 175

Asn Ile Val Glu Asn Asn Thr Val Phe Tyr Lys Lys Glu Asp Ala Glu
                180                 185                 190

Asn Gly Met Gly Thr Met Thr Glu Ile Trp Phe Gln Pro Phe Leu Thr
            195                 200                 205

Tyr Lys Tyr Asp Gln Phe Tyr Ile Asp Pro Ala Ile Glu Leu Met Lys
210                 215                 220

Cys Leu Ile Lys Ser Leu Tyr Phe Leu Tyr Gly Ile Lys Pro Ser Asp
225                 230                 235                 240

Asp Leu Val Val Pro Tyr Arg Leu Arg Asn Glu Leu Glu Asn Ile Glu
                245                 250                 255

Tyr Ser Gln Leu Asp Ile Val Asp Leu Leu Val Ser Gly Gly Ile Asp
                260                 265                 270

Pro Lys Phe Ile Asn Thr Asp Pro Tyr Trp Phe Ile Asp Asn Tyr Phe
            275                 280                 285

Ser Asn Ala Lys Lys Met Phe Glu Asp His Arg Asn Ile Tyr Glu Thr
290                 295                 300

Glu Ile Glu Gly Asn Asn Ala Ile Gly Asn Asp Ile Lys Leu Arg Leu
305                 310                 315                 320

Lys Gln Lys Phe Arg Ile Asn Ile Asn Asp Ile Trp Glu Leu Asn Leu
                325                 330                 335

Asn Tyr Phe Ser Lys Glu Phe Asn Ile Met Met Pro Asp Arg Phe Asn
                340                 345                 350

Asn Ala Leu Lys His Phe Tyr Arg Lys Gln Tyr Lys Ile Asp Tyr
            355                 360                 365

Pro Glu Asn Tyr Ser Ile Asn Gly Phe Val Asn Gly Gln Ile Asn Ala
370                 375                 380

Gln Leu Ser Leu Ser Asp Arg Asn Gln Asp Ile Ile Asn Lys Pro Glu
385                 390                 395                 400

Glu Ile Ile Asn Leu Leu Asn Glu Asn Asn Val Leu Leu Met Arg Ser
                405                 410                 415

Asn Ile Tyr Gly Asp Gly Leu Lys Ser Thr Val Asp Asp Phe Tyr Ser
                420                 425                 430

Asn Tyr Lys Ile Pro Tyr Asn Arg Ala Tyr Glu Tyr His Phe Asn Asn
            435                 440                 445

Ser Asn Asp Ser Ser Leu Asp Asn Val Asn Ile Gly Val Ile Asp Asn
450                 455                 460

Ile Pro Glu Ile Ile Asp Val Asn Pro Tyr Lys Glu Asn Cys Asp Lys
465                 470                 475                 480
```

```
Phe Ser Pro Val Gln Lys Ile Thr Ser Thr Arg Glu Ile Asn Thr Asn
                485                 490                 495

Ile Pro Trp Pro Ile Asn Tyr Leu Gln Ala Gln Asn Thr Asn Asn Glu
            500                 505                 510

Lys Phe Ser Leu Ser Ser Asp Phe Val Glu Val Ser Ser Lys Asp
        515                 520                 525

Lys Ser Leu Val Tyr Ser Phe Leu Ser Asn Val Met Phe Tyr Leu Asp
    530                 535                 540

Ser Ile Lys Asp Asn Ser Pro Ile Asp Thr Asp Lys Lys Tyr Tyr Leu
545                 550                 555                 560

Trp Leu Arg Glu Ile Phe Arg Asn Tyr Ser Phe Asp Ile Thr Ala Thr
                565                 570                 575

Gln Glu Ile Asn Thr Asn Cys Gly Ile Asn Lys Val Val Thr Trp Phe
            580                 585                 590

Gly Lys Ala Leu Asn Ile Leu Asn Thr Ser Asp Ser Phe Val Glu Glu
        595                 600                 605

Phe Gln Asn Leu Gly Pro Ser Ser Leu Ile Asn Lys Lys Glu Asn Leu
    610                 615                 620

Ser Met Pro Ile Ile Glu Ile Tyr Glu Ile Pro Asn Asp Met Leu Gly
625                 630                 635                 640

Leu Pro Leu Asn Asp Leu Asn Glu Lys Leu Phe Asn Ile Tyr Ser Lys
                645                 650                 655

Asn Thr Ala Tyr Phe Lys Lys Ile Tyr Tyr Asn Phe Leu Asp Gln Trp
            660                 665                 670

Trp Thr Gln Tyr Tyr Ser Gln Tyr Phe Asp Leu Ile Cys Met Ala Lys
        675                 680                 685

Arg Ser Val Leu Ala Gln Glu Thr Leu Ile Lys Arg Ile Ile Gln Lys
    690                 695                 700

Lys Leu Ser Tyr Leu Ile Gly Asn Ser Asn Ile Ser Ser Asp Asn Leu
705                 710                 715                 720

Ala Leu Met Asn Leu Thr Thr Thr Asn Thr Leu Arg Asp Ile Ser Asn
                725                 730                 735

Glu Ser Gln Ile Ala Met Asn Asn Val Asp Ser Phe Leu Asn Asn Ala
            740                 745                 750

Ala Ile Cys Val Phe Glu Ser Asn Ile Tyr Pro Lys Phe Ile Ser Phe
        755                 760                 765

Met Glu Gln Cys Ile Asn Asn Ile Asn Ile Lys Thr Lys Glu Phe Ile
    770                 775                 780

Gln Lys Cys Thr Asn Ile Asn Glu Asp Glu Lys Leu Gln Leu Ile Asn
785                 790                 795                 800

Gln Asn Val Phe Asn Ser Leu Asp Phe Glu Phe Leu Asn Ile Gln Asn
                805                 810                 815

Met Lys Ser Leu Phe Ser Glu Thr Ala Leu Leu Ile Lys Glu Glu
            820                 825                 830

Thr Trp Pro Tyr Glu Leu Val Leu Tyr Ala Phe Gln Glu Ser Gly Asn
        835                 840                 845

Asn Val Ile Gly Asp Ala Ser Gly Lys Asn Thr Ser Ile Glu Tyr Ser
    850                 855                 860

Lys Asp Ile Gly Leu Val Tyr Gly Ile Asn Ser Asp Ala Leu Tyr Leu
865                 870                 875                 880

Asn Gly Ser Asn Gln Ser Ile Ser Phe Ser Asn Asp Phe Phe Glu Asn
                885                 890                 895

Gly Leu Thr Asn Ser Phe Ser Ile Tyr Phe Trp Leu Arg Asn Leu Gly
```

```
                900             905             910
Lys Asp Thr Ile Lys Ser Lys Leu Ile Gly Ser Lys Glu Asp Asn Cys
            915             920             925
Gly Trp Glu Ile Tyr Phe Gln Asp Thr Gly Leu Val Phe Asn Met Ile
        930             935             940
Asp Ser Asn Gly Asn Glu Lys Asn Ile Tyr Leu Ser Asp Val Ser Asn
945             950             955             960
Asn Ser Trp His Tyr Ile Thr Ile Ser Val Asp Arg Leu Lys Glu Gln
                965             970             975
Leu Leu Ile Phe Ile Asp Asp Asn Leu Val Ala Asn Glu Ser Ile Lys
            980             985             990
Glu Ile Leu Asn Ile Tyr Ser Ser  Asn Ile Ile Ser Leu  Leu Ser Glu
                995            1000            1005
Asn Asn  Pro Ser Tyr Ile Glu  Gly Leu Thr Ile Leu  Asn Lys Pro
    1010            1015            1020
Thr Thr  Ser Gln Lys Val Leu  Ser Asn Tyr Phe Lys  Ala Leu Asn
    1025            1030            1035
Asn Ser  Tyr Ile Arg Asp Ser  Ser Glu Glu Arg Leu  Glu Tyr Asn
    1040            1045            1050
Lys Thr  Tyr Gln Leu Tyr Asn  Tyr Val Phe Ser Asp  Lys Pro Ile
    1055            1060            1065
Cys Glu  Val Lys Gln Asn Asn  Asn Ile Tyr Leu Thr  Ile Asn Asn
    1070            1075            1080
Thr Asn  Asn Leu Asn Leu Gln  Ala Ser Lys Phe Lys  Leu Leu Ser
    1085            1090            1095
Ile Asn  Pro Asn Lys Gln Tyr  Val Gln Lys Phe Asp  Glu Val Ile
    1100            1105            1110
Ile Ser  Ile Leu Asp Asn Met  Glu Lys Tyr Ile Asp  Ile Ser Glu
    1115            1120            1125
Asp Asn  Arg Leu Gln Leu Ile  Asp Asn Lys Asn Ser  Ala Lys Lys
    1130            1135            1140
Met Ile  Ile Ser Asn Asp Ile  Phe Ile Ser Asn Cys  Leu Thr Leu
    1145            1150            1155
Ser Cys  Gly Gly Lys Tyr Ile  Cys Leu Ser Met Lys  Asp Glu Asn
    1160            1165            1170
His Asn  Trp Met Ile Cys Asn  Asn Asp Met Ser Lys  Tyr Leu Tyr
    1175            1180            1185
Leu Trp  Ser Phe Lys
    1190
```